(12) United States Patent
Updyke et al.

(10) Patent No.: US 10,792,414 B2
(45) Date of Patent: Oct. 6, 2020

(54) UNIVERSAL PORTABLE MACHINE FOR ONLINE HEMODIAFILTRATION USING REGENERATED DIALYSATE

(71) Applicant: FRESENIUS MEDICAL CARE HOLDINGS, INC., Waltham, MA (US)

(72) Inventors: Palmer David Updyke, Walnut Creek, CA (US); Barry Fulkerson, Longmont, CO (US); Amaury De Leon De Leon, Irvine, CA (US); Michelle Bayly, Aliso Viejo, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 197 days.

(21) Appl. No.: 14/958,335

(22) Filed: Dec. 3, 2015

(65) Prior Publication Data

US 2016/0089485 A1 Mar. 31, 2016

Related U.S. Application Data

(63) Continuation of application No. 13/828,240, filed on Mar. 14, 2013, now abandoned.

(51) Int. Cl.
*A61M 1/36* (2006.01)
*A61M 1/34* (2006.01)
(Continued)

(52) U.S. Cl.
CPC ........ *A61M 1/3663* (2013.01); *A61M 1/1621* (2014.02); *A61M 1/1696* (2013.01);
(Continued)

(58) Field of Classification Search
None
See application file for complete search history.

(56) References Cited

U.S. PATENT DOCUMENTS 2,328,381 A   8/1943   Samuel
3,989,622 A   11/1976  Marantz et al.
(Continued)

FOREIGN PATENT DOCUMENTS

CN   1065799 A   11/1992
CN   1311700 A   9/2001
(Continued)

OTHER PUBLICATIONS

PCT International Search Report in corresponding International Patent Application PCT/US2008/85062, dated Mar. 20, 2009.
(Continued)

*Primary Examiner* — Jonathan M Peo
(74) *Attorney, Agent, or Firm* — Kilyk & Bowersox, P.L.L.C.

(57) ABSTRACT

Manifolds suitable for use in hemodialysis, hemofiltration, hemodiafiltration, and peritoneal dialysis are provided. One or more of the manifolds can include a manifold body and an external tube. The manifold body can include at least one conduit including a first conduit and at least one port including a first port in fluid communication with the first conduit. The external tube can be in fluid communication with the first port and can include a main segment, a first branch segment, and a second branch segment containing at least one bacterial filter. The first branch segment and/or second branch segment can include at least one flow restrictor. Dialysis machines, systems, and kits including one or more such manifolds are also provided, as are methods of performing hemodiafiltration using such manifolds.

6 Claims, 8 Drawing Sheets

(51) Int. Cl.
*A61M 1/16* (2006.01)
*A61M 1/28* (2006.01)

(52) U.S. Cl.
CPC .......... *A61M 1/342* (2013.01); *A61M 1/3413* (2013.01); *A61M 1/3465* (2014.02); *A61M 1/28* (2013.01); *A61M 1/3431* (2014.02); *A61M 2205/12* (2013.01); *A61M 2205/7518* (2013.01)

(56) References Cited

U.S. PATENT DOCUMENTS

| | | | |
|---|---|---|---|
| 4,037,596 A | 7/1977 | Lefevre et al. | |
| 4,071,444 A | 1/1978 | Ash et al. | |
| 4,141,836 A | 2/1979 | Schael | |
| 4,172,794 A | 10/1979 | Sigdell | |
| 4,190,047 A | 2/1980 | Jacobsen et al. | |
| 4,213,859 A | 7/1980 | Smakman et al. | |
| 4,247,393 A | 1/1981 | Wallace | |
| 4,261,830 A | 4/1981 | Schael et al. | |
| 4,267,834 A | 5/1981 | Barger et al. | |
| 4,311,587 A | 1/1982 | Nose et al. | |
| 4,347,136 A | 8/1982 | Friesen et al. | |
| 4,348,283 A | 9/1982 | Ash | |
| 4,368,737 A | 1/1983 | Ash | |
| 4,387,777 A | 6/1983 | Ash | |
| 4,402,694 A | 9/1983 | Ash et al. | |
| 4,403,984 A | 9/1983 | Ash et al. | |
| 4,413,988 A | 11/1983 | Klandt et al. | |
| 4,464,172 A | 8/1984 | Lichtenstein | |
| 4,464,179 A | 8/1984 | Barger et al. | |
| 4,469,593 A | 9/1984 | Ishihara et al. | |
| 4,498,902 A | 2/1985 | Ash et al. | |
| 4,559,039 A | 12/1985 | Ash et al. | |
| 4,568,366 A | 2/1986 | Frederick et al. | |
| 4,581,141 A | 4/1986 | Ash | |
| 4,626,243 A | 12/1986 | Singh et al. | |
| 4,661,246 A | 4/1987 | Ash | |
| 4,740,755 A | 4/1988 | Ogawa | |
| 4,777,953 A | 10/1988 | Ash et al. | |
| 4,854,322 A | 8/1989 | Ash et al. | |
| 4,914,819 A | 4/1990 | Ash | |
| 4,943,279 A | 7/1990 | Samiotes et al. | |
| 4,995,268 A | 2/1991 | Ash et al. | |
| 4,997,570 A | 3/1991 | Polaschegg | |
| 5,002,054 A | 3/1991 | Ash et al. | |
| 5,032,261 A | 7/1991 | Pyper | |
| 5,100,554 A | 3/1992 | Polaschegg | |
| 5,114,580 A | 5/1992 | Ahmad et al. | |
| 5,147,613 A | 9/1992 | Hellmann et al. | |
| 5,198,335 A | 3/1993 | Sekikawa et al. | |
| 5,211,643 A | 5/1993 | Reinhardt et al. | |
| 5,230,341 A | 7/1993 | Polaschegg | |
| 5,248,300 A | 9/1993 | Bryant et al. | |
| 5,277,820 A | 1/1994 | Ash | |
| 5,282,981 A | 2/1994 | Adams et al. | |
| 5,295,505 A | 3/1994 | Polaschegg et al. | |
| 5,304,349 A | 4/1994 | Polaschegg | |
| 5,308,315 A | 5/1994 | Khuri et al. | |
| 5,322,519 A | 6/1994 | Ash | |
| 5,385,005 A | 1/1995 | Ash | |
| D355,816 S | 2/1995 | Ash | |
| 5,405,315 A | 4/1995 | Khun et al. | |
| 5,409,477 A | 4/1995 | Caron et al. | |
| 5,445,630 A | 8/1995 | Richmond | |
| 5,460,493 A | 10/1995 | Deniega et al. | |
| 5,476,444 A | 12/1995 | Keeling et al. | |
| D370,531 S | 6/1996 | Ash et al. | |
| 5,536,412 A | 7/1996 | Ash | |
| 5,540,265 A | 7/1996 | Polaschegg | |
| 5,577,891 A | 11/1996 | Loughnane et al. | |
| 5,580,460 A | 12/1996 | Polaschegg | |
| 5,609,770 A | 3/1997 | Zimmerman et al. | |
| 5,614,677 A | 3/1997 | Wamsiedler et al. | |
| 5,616,305 A | 4/1997 | Mathieu | |
| 5,624,551 A | 4/1997 | Baumann et al. | |
| 5,632,897 A | 5/1997 | Mathieu | |
| 5,698,083 A | 12/1997 | Glass | |
| 5,711,883 A | 1/1998 | Folden | |
| 5,713,850 A | 2/1998 | Hellmann et al. | |
| 5,725,773 A | 3/1998 | Polaschegg | |
| 5,730,712 A * | 3/1998 | Falkvall ................ | A61M 1/16 210/321.8 |
| 5,769,811 A | 6/1998 | Stacey et al. | |
| 5,782,796 A | 7/1998 | Din et al. | |
| 5,794,669 A | 8/1998 | Polaschegg et al. | |
| 5,858,186 A | 1/1999 | Glass | |
| 5,868,933 A | 2/1999 | Patrick et al. | |
| 5,882,516 A | 3/1999 | Gross et al. | |
| 5,906,978 A | 5/1999 | Ash | |
| 5,919,369 A | 7/1999 | Ash | |
| 5,944,684 A | 8/1999 | Roberts et al. | |
| 5,947,953 A | 9/1999 | Ash et al. | |
| 5,989,438 A | 11/1999 | Fumiyama | |
| 6,042,561 A | 3/2000 | Ash et al. | |
| 6,156,007 A | 12/2000 | Ash | |
| 6,187,207 B1 | 2/2001 | Brauer | |
| 6,190,349 B1 | 2/2001 | Ash et al. | |
| 6,217,540 B1 | 4/2001 | Yazawa et al. | |
| 6,234,989 B1 | 5/2001 | Brierton et al. | |
| 6,254,567 B1 | 7/2001 | Treu et al. | |
| 6,264,680 B1 | 7/2001 | Ash | |
| 6,287,516 B1 | 9/2001 | Matson et al. | |
| 6,303,036 B1 * | 10/2001 | Collins ................. | A61M 1/342 210/143 |
| 6,331,252 B1 | 12/2001 | El Sayyid et al. | |
| 6,332,985 B1 | 12/2001 | Sherman et al. | |
| 6,348,162 B1 | 2/2002 | Ash | |
| 6,409,699 B1 | 6/2002 | Ash | |
| 6,471,872 B2 | 10/2002 | Kitaevich et al. | |
| 6,497,675 B1 | 12/2002 | Davankov | |
| 6,551,513 B2 | 4/2003 | Nikaido et al. | |
| 6,554,789 B1 | 4/2003 | Brugger et al. | |
| 6,565,749 B1 | 5/2003 | Hou et al. | |
| 6,572,576 B2 | 6/2003 | Brugger et al. | |
| 6,572,641 B2 | 6/2003 | Brugger et al. | |
| 6,579,253 B1 | 6/2003 | Burbank et al. | |
| 6,579,460 B1 | 6/2003 | Willis et al. | |
| 6,582,385 B2 | 6/2003 | Burbank et al. | |
| 6,589,482 B1 | 7/2003 | Burbank et al. | |
| 6,595,943 B1 | 7/2003 | Burbank | |
| 6,623,470 B2 | 9/2003 | Munis et al. | |
| 6,627,164 B1 | 9/2003 | Wong | |
| 6,638,477 B1 | 10/2003 | Treu et al. | |
| 6,638,478 B1 | 10/2003 | Treu et al. | |
| 6,649,063 B2 | 11/2003 | Brugger et al. | |
| 6,653,841 B1 | 11/2003 | Koerdt et al. | |
| 6,655,207 B1 | 12/2003 | Speldrich et al. | |
| 6,673,314 B1 | 1/2004 | Burbank et al. | |
| 6,690,280 B2 | 2/2004 | Citrenbaum et al. | |
| 6,702,561 B2 | 3/2004 | Stillig et al. | |
| 6,730,266 B2 | 5/2004 | Matson et al. | |
| 6,743,193 B2 | 6/2004 | Brugger et al. | |
| 6,764,460 B2 | 7/2004 | Dolecek et al. | |
| 6,802,821 B2 | 10/2004 | Jacobsen et al. | |
| 6,818,196 B2 | 11/2004 | Wong | |
| 6,830,553 B1 | 12/2004 | Burbank et al. | |
| 6,841,172 B1 | 1/2005 | Ash | |
| 6,852,090 B2 | 2/2005 | Burbank et al. | |
| 6,872,346 B2 | 3/2005 | Stillig | |
| 6,878,283 B2 | 4/2005 | Thompson | |
| 6,892,755 B2 | 5/2005 | Black | |
| 6,911,007 B2 | 6/2005 | Nier et al. | |
| 6,923,782 B2 | 8/2005 | O'Mahony et al. | |
| 6,955,655 B2 | 10/2005 | Burbank et al. | |
| 6,958,049 B1 | 10/2005 | Ash | |
| 6,960,179 B2 | 11/2005 | Gura | |
| 6,960,328 B2 | 11/2005 | Bortun et al. | |
| 6,979,309 B2 | 12/2005 | Burbank et al. | |
| 6,989,101 B2 | 1/2006 | Cumberland et al. | |
| 7,004,924 B1 | 2/2006 | Brugger et al. | |
| 7,007,549 B2 | 3/2006 | Kwon et al. | |
| 7,018,327 B1 | 3/2006 | Conti | |
| 7,033,498 B2 | 4/2006 | Wong | |

(56) References Cited

U.S. PATENT DOCUMENTS

| | | |
|---|---|---|
| 7,040,142 B2 | 5/2006 | Burbank |
| 7,087,033 B2 | 8/2006 | Brugger et al. |
| 7,101,519 B2 | 9/2006 | Wong |
| 7,112,273 B2 | 9/2006 | Weigel et al. |
| 7,115,095 B2 | 10/2006 | Eigler et al. |
| 7,135,156 B2 | 11/2006 | Hai et al. |
| 7,144,386 B2 | 12/2006 | Korkor et al. |
| 7,147,613 B2 | 12/2006 | Burbank et al. |
| 7,169,303 B2 | 1/2007 | Sullivan et al. |
| 7,175,809 B2 | 2/2007 | Gelfand et al. |
| 7,208,092 B2 | 4/2007 | Micheli |
| 7,214,312 B2 | 5/2007 | Brugger et al. |
| 7,226,538 B2 | 6/2007 | Brugger et al. |
| 7,241,272 B2 | 7/2007 | Karoor et al. |
| 7,252,767 B2 | 8/2007 | Bortun et al. |
| 7,267,658 B2 | 9/2007 | Treu et al. |
| 7,273,465 B2 | 9/2007 | Ash |
| 7,276,042 B2 | 10/2007 | Polaschegg et al. |
| 7,300,413 B2 | 11/2007 | Burbank et al. |
| 7,303,683 B2 | 12/2007 | Cumberland |
| 7,309,323 B2 | 12/2007 | Gura et al. |
| 7,337,674 B2 | 3/2008 | Burbank et al. |
| 7,338,460 B2 | 3/2008 | Burbank et al. |
| 7,347,849 B2 | 3/2008 | Brugger et al. |
| 7,494,590 B2 | 2/2009 | Felding et al. |
| 7,614,506 B2 | 11/2009 | Mitchell et al. |
| 7,615,152 B2 | 11/2009 | Tanner et al. |
| 7,631,562 B1 | 12/2009 | Speldrich |
| 7,690,396 B2 | 4/2010 | Oh et al. |
| 7,736,507 B2 | 6/2010 | Wong |
| 7,867,214 B2 | 1/2011 | Childers et al. |
| 7,901,376 B2 | 3/2011 | Steck et al. |
| 7,922,008 B2 | 4/2011 | Bahm et al. |
| 7,922,686 B2 | 4/2011 | Childers et al. |
| 7,922,911 B2 | 4/2011 | Micheli |
| 8,021,319 B2 | 9/2011 | Delnevo et al. |
| 8,034,235 B2 | 10/2011 | Rohde et al. |
| 8,062,513 B2 | 11/2011 | Yu et al. |
| 8,066,658 B2 | 11/2011 | Karoor et al. |
| 8,070,707 B2 | 12/2011 | Gelfand et al. |
| 8,075,509 B2 | 12/2011 | Molducci et al. |
| 8,078,333 B2 | 12/2011 | Kienman et al. |
| 8,080,161 B2 | 12/2011 | Ding et al. |
| 8,096,969 B2 | 1/2012 | Roberts et al. |
| 8,105,260 B2 | 1/2012 | Tonelli et al. |
| 8,105,487 B2 | 1/2012 | Fulkerson et al. |
| 8,187,250 B2 | 5/2012 | Roberts et al. |
| 8,197,439 B2 | 6/2012 | Wang et al. |
| 8,202,428 B2 | 6/2012 | Hellmann et al. |
| 8,219,982 B2 | 7/2012 | Harkanyi et al. |
| 8,220,643 B2 | 7/2012 | Eisen |
| 8,267,308 B2 | 9/2012 | Devergne et al. |
| 8,298,167 B2 | 10/2012 | Peters et al. |
| 8,303,807 B2 | 11/2012 | Zhang |
| 8,323,492 B2 | 12/2012 | Childers et al. |
| 8,328,758 B2 | 12/2012 | Childers et al. |
| 8,329,030 B2 | 12/2012 | Childers et al. |
| 8,357,113 B2 | 1/2013 | Childers et al. |
| 8,361,023 B2 | 1/2013 | Bedingfield |
| 8,512,553 B2 | 8/2013 | Cicchello et al. |
| 2001/0037964 A1 | 11/2001 | Won et al. |
| 2002/0045851 A1 | 4/2002 | Suzuki et al. |
| 2002/0068364 A1 | 6/2002 | Arai et al. |
| 2002/0085951 A1 | 7/2002 | Gelfand et al. |
| 2002/0104800 A1 | 8/2002 | Collins et al. |
| 2003/0000884 A1 | 1/2003 | Hamlin et al. |
| 2003/0098276 A1 | 5/2003 | Carlson |
| 2003/0114787 A1 | 6/2003 | Gura |
| 2004/0019312 A1 | 1/2004 | Childers et al. |
| 2004/0050789 A1 | 3/2004 | Ash |
| 2004/0116095 A1 | 6/2004 | Pedersen et al. |
| 2004/0164006 A1 | 8/2004 | Brown et al. |
| 2004/0167465 A1 | 8/2004 | Mihai et al. |
| 2005/0000883 A1 | 1/2005 | Kouters et al. |
| 2005/0070837 A1 | 3/2005 | Ferrarini et al. |
| 2005/0131331 A1* | 6/2005 | Kelly ............... A61M 1/34 604/4.01 |
| 2005/0131332 A1 | 6/2005 | Kelley et al. |
| 2005/0133439 A1 | 6/2005 | Blickhan |
| 2005/0236330 A1 | 10/2005 | Nier et al. |
| 2006/0122552 A1 | 6/2006 | O'Mahony |
| 2006/0226086 A1 | 10/2006 | Robinson et al. |
| 2007/0112297 A1 | 5/2007 | Plahey et al. |
| 2007/0131296 A1 | 6/2007 | Schinazi et al. |
| 2007/0158267 A1 | 7/2007 | Micheli |
| 2007/0161113 A1 | 7/2007 | Ash |
| 2007/0213654 A1 | 9/2007 | Lundtveit et al. |
| 2007/0213665 A1 | 9/2007 | Curtin et al. |
| 2007/0278141 A1 | 12/2007 | Patera et al. |
| 2008/0029173 A1 | 2/2008 | Diperna |
| 2008/0041136 A1 | 2/2008 | Kopelman et al. |
| 2008/0041792 A1 | 2/2008 | Crnkovich et al. |
| 2008/0164214 A1 | 7/2008 | Lerner et al. |
| 2008/0230450 A1 | 9/2008 | Burbank et al. |
| 2008/0253427 A1 | 10/2008 | Kamen et al. |
| 2008/0258735 A1 | 10/2008 | Quackenbush et al. |
| 2009/0007862 A1 | 1/2009 | Nakamura et al. |
| 2009/0008306 A1* | 1/2009 | Cicchello ........... A61M 1/1694 210/85 |
| 2009/0076434 A1 | 3/2009 | Mischelevich et al. |
| 2009/0095679 A1 | 4/2009 | Demers et al. |
| 2009/0101552 A1 | 4/2009 | Fulkerson et al. |
| 2009/0101577 A1 | 4/2009 | Fulkerson et al. |
| 2009/0113335 A1 | 4/2009 | Sandoe et al. |
| 2009/0114037 A1 | 5/2009 | Smith |
| 2009/0120864 A1 | 5/2009 | Fulkerson et al. |
| 2009/0124963 A1 | 5/2009 | Hogard et al. |
| 2009/0127193 A1 | 5/2009 | Updyke et al. |
| 2009/0173682 A1 | 7/2009 | Robinson et al. |
| 2009/0188854 A1 | 7/2009 | Farrelly et al. |
| 2009/0223880 A2 | 9/2009 | Zhang et al. |
| 2009/0312694 A1 | 12/2009 | Bedingfield et al. |
| 2009/0314707 A1 | 12/2009 | Karoor et al. |
| 2010/0010430 A1 | 1/2010 | Micheli |
| 2010/0078387 A1 | 4/2010 | Wong |
| 2010/0100027 A1 | 4/2010 | Schilthuizen et al. |
| 2010/0114012 A1 | 5/2010 | Sandford et al. |
| 2010/0116048 A1 | 5/2010 | Fulkerson et al. |
| 2010/0116740 A1 | 5/2010 | Fulkerson et al. |
| 2010/0137782 A1 | 6/2010 | Jansson et al. |
| 2010/0140149 A1 | 6/2010 | Fulkerson et al. |
| 2010/0179464 A1 | 7/2010 | Smith |
| 2010/0184198 A1 | 7/2010 | Joseph et al. |
| 2010/0234786 A1 | 9/2010 | Fulkerson et al. |
| 2010/0252490 A1 | 10/2010 | Fulkerson et al. |
| 2010/0312172 A1 | 12/2010 | Hoffman |
| 2010/0312174 A1 | 12/2010 | Hoffman |
| 2010/0331754 A1 | 12/2010 | Fulkerson et al. |
| 2011/0000832 A1 | 1/2011 | Kelly et al. |
| 2011/0009798 A1 | 1/2011 | Kelly et al. |
| 2011/0017665 A1 | 1/2011 | Updyke et al. |
| 2011/0054378 A1 | 3/2011 | Fulkerson |
| 2011/0071465 A1 | 3/2011 | Wang et al. |
| 2011/0093294 A1 | 4/2011 | Elahi et al. |
| 2011/0155667 A1 | 6/2011 | Charest et al. |
| 2011/0171713 A1 | 7/2011 | Bluchel et al. |
| 2011/0184340 A1 | 7/2011 | Tan et al. |
| 2011/0272337 A1 | 11/2011 | Palmer |
| 2011/0297593 A1 | 12/2011 | Kelly et al. |
| 2011/0297598 A1 | 12/2011 | Lo et al. |
| 2011/0297599 A1 | 12/2011 | Lo et al. |
| 2011/0303588 A1 | 12/2011 | Kelly et al. |
| 2011/0303590 A1 | 12/2011 | Childers et al. |
| 2011/0303598 A1 | 12/2011 | Lo et al. |
| 2011/0315611 A1* | 12/2011 | Fulkerson ........... A61M 1/3639 210/96.2 |
| 2012/0031826 A1 | 2/2012 | Childers et al. |
| 2012/0037550 A1 | 2/2012 | Childers et al. |
| 2012/0043279 A1 | 2/2012 | Kelly et al. |
| 2012/0073365 A1 | 3/2012 | Fulkerson et al. |
| 2012/0090706 A1 | 4/2012 | Fulkerson et al. |
| 2012/0103885 A1 | 5/2012 | Robinson et al. |
| 2012/0172736 A1 | 7/2012 | Zhang et al. |
| 2012/0190919 A1 | 7/2012 | Phillips et al. |

(56) References Cited

U.S. PATENT DOCUMENTS

| | | |
|---|---|---|
| 2012/0204968 A1 | 8/2012 | Fulkerson et al. |
| 2012/0220926 A1 | 8/2012 | Soykan et al. |
| 2012/0248017 A1 | 10/2012 | Beiriger et al. |
| 2012/0265117 A1 | 10/2012 | Fava et al. |
| 2012/0265164 A1 | 10/2012 | Reiterer et al. |
| 2012/0266965 A1 | 10/2012 | Hariharesan et al. |
| 2012/0271227 A1 | 10/2012 | Roberts et al. |
| 2012/0273354 A1 | 11/2012 | Orhan et al. |
| 2012/0280154 A1 | 11/2012 | Smith |
| 2013/0004593 A1 | 1/2013 | Kloeffel et al. |
| 2013/0008852 A1 | 1/2013 | Eisen |
| 2014/0263062 A1 | 9/2014 | Updlcye et al. |
| 2014/0276371 A1 | 9/2014 | Fresenius |
| 2016/0038666 A1 | 2/2016 | Kelly et al. |

FOREIGN PATENT DOCUMENTS

| | | |
|---|---|---|
| CN | 1509202 A | 6/2004 |
| CN | 2746916 Y | 12/2005 |
| CN | 101394876 A | 3/2009 |
| CN | 101678161 A | 3/2010 |
| CN | 101986776 A | 3/2011 |
| CN | 102389594 A | 3/2012 |
| EP | 0771569 A2 | 5/1997 |
| WO | 2009073567 A1 | 6/2009 |

OTHER PUBLICATIONS

PCT International Search Report in corresponding International Patent Application PCT/US2010/29500, dated Jul. 2, 2010.

PCT International Search Report and Written Oopinion in corresponding International Patent Application PCT/US2014/025469, dated Jun. 11, 2014.

Non-Final Office Action for U.S. Appl. No. 13/828,240 dated Jul. 30, 2014, including Form PTO-892.

Non-Final Office Action for U.S. Appl. No. 13/828,240 dated Jul. 27, 2015, including Form PTO-892.

Non-Final Office Action for U.S. Appl. No. 13/828,636 dated Sep. 17, 2015, including Form PTO-892.

Final Office Action for U.S. Appl. No. 13/828,636, dated Feb. 4, 2016, including Form PTO-892.

Final Office Action for U.S. Appl. No. 13/828,240, dated Jan. 12, 2016, including Form PTO-892.

Office Action for Chinese Patent Application No. 201480014881.0, issued by the Chinese State Intellectual Property Office (SIPO), dated May 5, 2016, including search report and English-language translation, 18 pages.

Office Action for Canadian Patent Application No. 2,899,641, issued by the Canadian Intellectual Property Office (CIPO), dated May 27, 2016, including Examination Search Report dated May 18, 2016.

Office Action for Chinese Patent Application No. 201480014881.0, issued by the Chinese State Intellectual Property Office (SIPO), dated Nov. 9, 2015, 5 pages.

Office Action for Canadian Patent Application No. 2,899,641, issued by the Canadian Intellectual Property Office (CIPO), dated Dec. 7, 2016, including Examination Search Report dated Nov. 29, 2016, 3 pages.

\* cited by examiner

UNIVERSAL PORTABLE MACHINE FOR ONLINE HEMODIAFILTRATION USING REGENERATED DIALYSATE

CROSS-REFERENCE TO RELATED APPLICATION

This application is a Continuation of U.S. patent application Ser. No. 13/828,240, filed Mar. 14, 2013, which is incorporated herein in its entirety by reference.

FIELD OF THE INVENTION

The present invention relates to materials, machines, systems, and methods for conducting hemodialysis, hemofiltration, hemodiafiltration, and peritoneal dialysis.

BACKGROUND OF THE INVENTION

In hemofiltration (HF), solute clearance is achieved through convection, that is, solutes are pulled, along with water, down a pressure gradient. Hemodiafiltration (HDF) combines the concentration-based diffusion of hemodialysis (HD) with hemofiltration. HF generally provides better removal of large molecular weight solutes, improved clearance of low molecular weight uremic toxins, and better cardiovascular stability and blood pressure control than HD. HF can be especially beneficial to long term dialysis patients who are likely to be on dialysis for a long time, and for larger patients in whom it is not possible to achieve sufficient Kt/V with HD. Intradialytic symptoms are often reduced with HF, and residual renal function can be better preserved with HDF. HDF also appears to have beneficial effects on mortality and hospitalization.

The ultrafiltration (UF) aspect of HDF results in loss of fluid. This fluid loss can be made up with replacement fluid, which should be ultrapure, with minimal contamination, because the fluid is placed directly into the blood stream. The reliance on ultrapure water has limited the portability of HDF systems. It would be desirable to have a machine that would minimize the amount of water or bagged fluid that is currently used for HDF. The use of highly permeable and high flux membranes, high blood flows, and accurate control of volume replacement also make HDF a complicated undertaking. Accordingly, there exists a need for better materials and methods for conducting HDF.

SUMMARY OF THE PRESENT INVENTION

A feature of the present invention is to provide materials and methods for performing hemodiafiltration, as well as hemodialysis, hemofiltration, and peritoneal dialysis.

Another feature of the present invention is to utilize purified dialysate as replacement (ultrafiltration) fluid into the bloodstream to minimize or avoid the use of dedicated, ultrapure replacement fluid, or reliance on additional, cumbersome water purification systems.

Yet another feature of the present invention is to provide a more portable hemodiafiltration system.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, a manifold suitable for use in hemodialysis, hemofiltration, hemodiafiltration, and peritoneal dialysis, is provided. The manifold can include a manifold body and an external tube. For example, the manifold can include a manifold body, at least one pump tube including a first pump tube, and at least one external tube including a first external tube. The manifold body can include at least one conduit including a first conduit and at least one port including a first port in fluid communication with the first conduit. The external tube can be in fluid communication with the first port and can include a main segment, a first branch segment, and a second branch segment containing at least one bacterial filter. The first branch segment and/or second branch segment can include at least one flow restrictor. The second branch segment can contain any number or type of bacterial filters.

In accordance with the present invention, a dialysis machine is provided that can include a housing, a receptacle mounted on the housing and configured to accept a manifold, a manifold operatively engaged with the receptacle, and at least one flow restrictor mounted on the housing and configured for accepting at least one of the first branch segment and the second branch segment of the manifold. The at least one flow restrictor can include a first flow restrictor configured to accept the first branch segment and a second flow restrictor configured for accepting the second branch segment. The at least one flow restrictor can include a static flow restrictor, a dynamic (variable) flow restrictor, or both.

A kit including the manifold is also provided. The kit can further include a dialyzer, tubing, a bacterial filter, and other components suitable for hemodialysis, hemofiltration, hemodiafiltration, and/or peritoneal dialysis. The present invention also provides a dialysis system, and the dialysis system can include a dialysis machine, a manifold operatively engaged with the dialysis machine, and a supply of dialysate in fluid communication with the manifold. The dialysis system can be configured to perform one or more of hemodialysis, hemofiltration, hemodiafiltration, and peritoneal dialysis.

In accordance with the present invention, a method of performing hemodiafiltration on a patient, is provided. The method can include one or more of the following steps. A flow of dialysate can be pumped through a dialysate circuit. A flow of blood can be pumped through an extracorporeal blood circuit. The flow of dialysate in the dialysate circuit can be restricted to divert a portion of the flow of dialysate into the extracorporeal blood circuit. The portion can be passed through the at least one bacterial filter before the portion enters the blood circuit. The flow restriction can be static, varied, or both.

It is to be understood that both the foregoing general description and the following detailed description are exemplary and explanatory only and are intended to provide a further explanation of the present invention, while not limiting the invention.

BRIEF DESCRIPTION OF THE DRAWINGS

The accompanying drawings, which are incorporated in and constitute a part of this application, illustrate some of the embodiments of the present invention. The drawings, together with the description, serve to explain the principles of the present invention.

DETAILED DESCRIPTION OF THE PRESENT INVENTION

Figure 1:
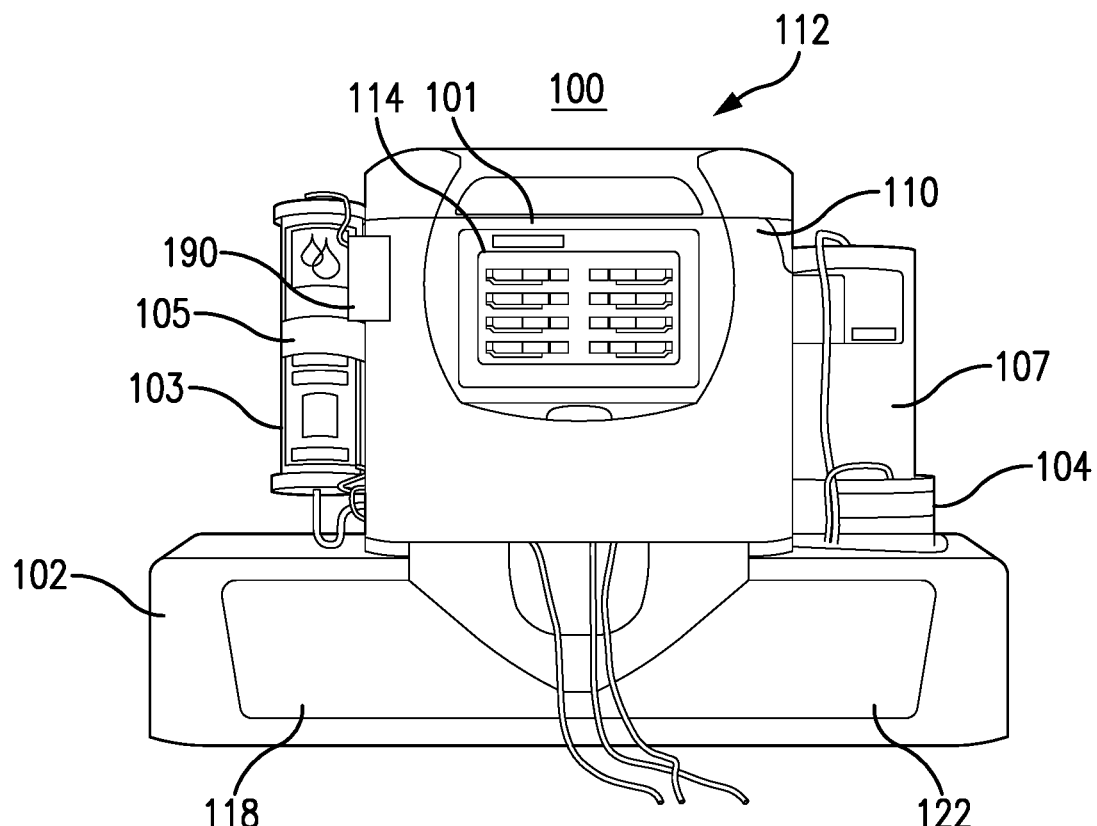
FIG. 1 is a front view of a dialysis system in accordance with the present invention.

In accordance with the present invention, a manifold suitable for use in hemodialysis, hemofiltration, hemodiafiltration, and peritoneal dialysis is provided. The manifold can include a manifold body and an external tube. The manifold body can include at least one conduit including a first conduit, and at least one port including a first port in fluid communication with the first conduit. The external tube can be in fluid communication with the first port and can include a main segment, a first branch segment, and a second branch segment including at least one bacterial filter. Any number or type of bacterial filters can be used. For example, the second branch segment can include at least two bacterial filters.

The manifold including the external tube can contain any number or type of flow restrictor and/or be restricted by one or more external flow restrictors. For example, at least one of the first branch segment and the second branch segment can contain a flow restrictor. The first branch segment can include a first flow restrictor and the second branch segment can include a second flow restrictor. The second flow restrictor can be located between the at least one bacterial filter and the main segment. The flow restrictor can be a static flow restrictor, a variable flow restrictor, or a combination thereof. One or more valve can act as a flow restrictor. Examples of flow restrictors that can be used include those described in U.S. Pat. Nos. 4,037,596, 4,267,834, 4,464,179, 4,626,243, 5,248,300, 5,282,981, 5,409,477, U.S. Pat. No. 6,655,207 B1, U.S. Pat. No. 6,892,755 B2, U.S. Pat. No. 7,018,327 B1, U.S. Pat. No. 7,631,562 B1, and U.S. Pat. No. 7,690,396 B2, which are incorporated herein by reference in their entireties. Examples of flow restrictors that can be used also include those described in U.S. Patent Application Publications Nos. US 2004/0116905 A1, US 2007/0131296 A1, US 2008/0017260 A1, US 2008/0029173 A1, US 2012/0190919 A1, US 2012/0265164 A1, and US 2012/0266965 A1, which are also incorporated herein by reference in their entireties.

The manifold can be configured to engage a dialysis machine and the first conduit can be configured to join a first circuit. The dialysis machine can have at least one pump and the manifold can be configured to engage the at least one pump to allow for a movement of a first fluid in the first circuit. The at least one pump can include any desired type of pump, for example, a peristaltic pump. The manifold can include a second conduit and be configured to join a second circuit. The dialysis machine can have a second pump and the manifold can be configured to engage the second pump to allow for movement of a second fluid in the second circuit. The external tube can be in fluid communication with the first and second conduits. The second branch segment can contain a valve between the at least one bacterial filter and the main segment. The first circuit can be a dialysate circuit and the second circuit can be an extracorporeal blood circuit, or vice versa. The manifold can further include a dialyzer in fluid communication with the first branch segment. The dialyzer can be separate from the manifold body.

In accordance with the present invention, a dialysis machine is provided that can include a housing, a receptacle mounted on the housing and configured to accept a manifold of the present invention, a manifold of the present invention operatively engaged with the receptacle, and at least one flow restrictor mounted on the housing and configured for accepting at least one of the first branch segment and the second branch segment of the manifold. The at least one flow restrictor can include a first flow restrictor configured to accept the first branch segment and a second flow restrictor configured for accepting the second branch segment. The at least one flow restrictor can include a static flow restrictor, a dynamic (variable) flow restrictor, or both.

A kit including the manifold as described herein, is also provided. The kit can further include a dialyzer, tubing, a bacterial filter, and other components suitable for hemodialysis, hemofiltration, hemodiafiltration, and/or peritoneal dialysis. The components can be preassembled (connected), separate, or partially connected, in the kit. Components can be coded using, for example, colors, letters, numbers, barcodes, RFID tags, or a combination thereof, to aid in the assembly of the components and installation on a dialysis machine to form a dialysis system. One or more components of the kit can be disposable and/or reusable. In some cases, the entire kit can comprise disposable components.

The present invention also provides a dialysis system. The dialysis system can include a dialysis machine, and a manifold operatively engaged with the dialysis machine. A supply of dialysate can be provided in fluid communication with the manifold. The dialysis system can be configured to perform one or more of hemodialysis, hemofiltration, hemodiafiltration, and peritoneal dialysis.

In accordance with the present invention, a manifold is provided that is suitable for use in one or more of hemodialysis, hemofiltration, hemodiafiltration, and peritoneal dialysis. Kits, machines, and systems including the manifold are also provided. The manifold can include a manifold body, at least one pump tube including a first pump tube, and at least one external tube including a first external tube. The manifold body can comprise a first transom having a first edge, and second and third edges that are substantially parallel to the first edge. The manifold can comprise a trunk that is substantially perpendicular to and adjacent the first transom, and a second transom. The second transom can be substantially perpendicular to and adjacent the trunk, and substantially parallel to the first transom. The second transom can include a fourth edge, and fifth and sixth edges that are substantially parallel to the first, second, and third edges. The manifold can contain one or more ports. For example, a plurality of ports that can be arrayed along the fourth edge. The plurality of ports can include at least a first port and a second port. A third port can be located on the second edge, and a fourth port can be located on the fifth edge. A first conduit can be located in the second transom in fluid communication with the first and fourth ports. A second conduit can be located in the first transom and in fluid communication with the second and third ports. The first pump tube can be in fluid communication with the third and fourth ports.

The first external tube of the manifold can be in fluid communication with the second port. The first external tube can include a main segment, a first branch segment, and a second branch segment. At least one of the first branch segment and the second branch segment can contain a flow restrictor. The first branch segment can contain a first flow restrictor and the second branch segment can contain a second flow restrictor. The second flow restrictor can be located between the at least one bacterial filter and the main segment. The flow restrictor can include a static flow restrictor, a dynamic flow restrictor, or both. The second branch segment can include at least one bacterial filter. The second branch segment can include a valve between the at least one bacterial filter and the main segment. The manifold can further include a dialyzer in fluid communication with the first branch segment. The dialyzer can be separate from the manifold body.

The manifold can be configured to engage a dialysis machine and the first conduit can be configured to join a first circuit. The dialysis machine can have at least one pump and the manifold can be configured to engage the at least one pump with the first pump tube to allow for a movement of a first fluid in the first circuit. The at least one pump can be any desired type of pump, for example, a peristaltic pump. The manifold can include a second pump tube in fluid communication with a fifth port on the second edge and a sixth port on the fifth edge, and the second pump tube can be configured to join a second circuit. The dialysis machine can have a second pump and the manifold can be configured to engage the second pump with the second pump tube to allow for movement of a second fluid in the second circuit. The external tube of the manifold can be in fluid communication with the first and second circuits. The first circuit can be a dialysate circuit and the second circuit can be an extracorporeal blood circuit, or vice versa.

In accordance with the present invention, a method of performing hemodiafiltration on a patient is provided. The method can include one or more of the following steps. A flow of dialysate can be pumped through a dialysate circuit. A flow of blood can be pumped through an extracorporeal blood circuit. The flow of dialysate in the dialysate circuit can be restricted to divert a portion of the flow of dialysate into the extracorporeal blood circuit. The portion can be passed through the at least one bacterial filter before the portion enters the blood circuit. The flow restriction can be static, varied, or both.

The dialysate circuit used in the circuit can include a branched conduit containing a main segment, a first branch segment, and a second branch segment. The second branch segment can carry the portion and be in fluid communication with the extracorporeal blood circuit. The restricting can include restricting the flow of dialysate in at least one of the first branch segment and the second branch segment. The restricting can include restricting the flow of dialysate in both the first branch segment and the second branch segment.

At least one of the flow of dialysate and the flow of blood can be pumped through a manifold engaged with a dialysis machine. The method can include engaging the manifold with the dialysis machine. At least one of pumping the flow of dialysate and pumping the flow of blood can include the use of at least one peristaltic pump. The dialysate circuit used in the method can contain a sorbent cartridge capable of regenerating the dialysate. The method can include pumping an electrolyte solution into the dialysate circuit. The pumping of the flow of dialysate and the pumping of the flow of blood can include pumping through at least one dialyzer.

The bacterial filter used in the method can include at least one dialyzer. For example, any of the bacterial filters described in U.S. Pat. Nos. 4,311,587, 4,347,136, 4,568,366, 5,868,933, U.S. Pat. No. 6,565,749 B2, U.S. Pat. No. 6,989,101 B2, U.S. Pat. No. 7,303,683 B2, U.S. Pat. No. 7,614,506 B2, U.S. Pat. No. 7,615,152 B2, and U.S. Pat. No. 7,922,008 B2 can be used, and all of these patents are incorporated herein by reference in their entireties. The bacterial filters described in U.S. Patent Application Publications Nos. US 2001/0037964 A1, US 2003/0000884 A1, US 2003/0098276 A1, US 2004/0164006, US 2005/0000883 A1, US 2007/0278141 A1, US 2008/0164214 A1, and US 2009/0188854 A1 can be used, and all of these publications are incorporated herein by reference in their entireties.

A dialyzer can be chosen from any suitable dialyzer compatible with the present methods, manifolds, machines, and systems of the present invention. A polysulfone dialyzer can be used. For example, the dialyzer can be an F180PSD, an F180NRE, an Optiflux®, a Hemaflow™, or an Ultraflux dialyzer available from Fresenius Medical Care North America, Waltham, Mass. The dialyzers described in U.S. Pat. Nos. 4,141,836, 4,172,794, 4,261,830, 5,882,516, U.S. Pat. No. 6,802,821 B2, U.S. Pat. No. 6,911,007 B2, U.S. Pat. No. 8,202,428 B2, and U.S. Pat. No. 8,303,807 B2 can be used, all of which patents are incorporated herein by reference in their entireties. The dialyzers described in U.S. Patent Application Publications Nos. US 2005/0236330 A1, US 2009/007862 A1, US 2009/0223880 A1, US 2012/0172736 A1, and US 2013/0004593 A1 can be used, and all of these publications are incorporated herein by reference in their entireties. An ion-rejecting dialyzer membrane can be used, which can reduce or eliminate the need for added electrolytes and, accordingly, increase portability.

A sorbent cartridge for use in the present invention can contain one or more of activated carbon, urease, zirconium phosphate, zirconium carbonate, and zirconium oxide. Any suitable sorbent cartridge can be used. For example, a HISORB® or HISORB®+ sorbent cartridge available from Renal Solutions, Inc. of Warrendale, Pa. can be used. The sorbents and sorbent cartridges described in U.S. Pat. Nos. 3,989,622, 4,190,047, 4,213,859, 4,247,393, 4,661,246, 5,277,820, 5,536,412, 5,919,369, 5,944,684, U.S. Pat. No. 6,348,162 B1, U.S. Pat. No. 6,960,179 B2, U.S. Pat. No. 7,033,498 B2, U.S. Pat. No. 7,169,303 B2, U.S. Pat. No. 7,208,092 B2, U.S. Pat. No. 7,736,507 B2, U.S. Pat. No. 7,867,214 B2, U.S. Pat. No. 7,922,686 B2, U.S. Pat. No. 7,922,911 B2, B2, U.S. Pat. No. 8,080,161 B2, U.S. Pat. No. 8,096,969 B2, U.S. Pat. No. 8,105,487 B2, U.S. Pat. No. 8,187,250 B2, U.S. Pat. No. 8,220,643 B2, and U.S. Pat. No. 8,357,113 B2 can be used, and all of these patents are incorporated herein by reference in their entireties. Sorbents and sorbent cartridges described in U.S. Patent Application Publications Nos. US 2002/0112609 A1, US 20030097086 A1, US 20030114787 A1, US 2004/0019312 A1, US 2004/0019320 A1, US 2004/0050789 A1, US 2004/0082903 A1, US 2005/0006296 A1, US 2005/0131332 A1, US 2007/0158267 A1, US 2007/0179431 A1, US 2007/0213665 A1, US 2009/0120864 A1, US 2009/0127193 A1, US 2009/

0264812 A1, US 2009/0314707 A1, US 2010/0010429 A1, US 2010/0010430 A1, US 2010/0078387 A1, US 2010/0100027 A1, US 2010/0114012 A1, US 2010/0217181 A1, US 2010/0230346 A1, US 2010/0312172 A1, US 2010/0312174 A1, US 2010/0314314 A1, US 2011/0017665 A1, US 2011/0155667 A1, US 2011/0171713 A1, US 2011/0184340 A1, US 2011/0272337 A1, US 20110297593 A1, US 2011/0303588 A1, US 2011/0303590 A1, US 20120248017 A1, US 2011/0315611 A1, US A1, US 2012/0271227 A1, or US 2013/0008852 A1 can be used, and all of these publications are incorporated herein by reference in their entireties. Dialysis regeneration can be achieved using other techniques instead of, or in addition to, sorbent-based techniques, to remove toxins or other species. For example, electrodialysis can be used as described in U.S. Patent Application Publications Nos. US 2012/0273354 A1 and US 2012/0220926 A1, which are incorporated herein by reference in their entireties.

U.S. Patent Application Publication Nos. US 2012/0280154 A1 and US 2010/0179464 A1, which are incorporated herein by reference in their entireties, describe valves and other elements that can be used in accordance with the present invention. US 2012/0204968 A1, which is incorporated herein by reference in its entirety, describes priming methods and other elements that can be used in accordance with the present invention. US 2012/0103885 A1, US 2012/0090706 A1, US 2010/0116740 A1, and US 2009/0173682 A1, which are incorporated herein by reference in their entireties, describe manifolds, ultrafiltration control means, and other elements that can be used in accordance with the present invention. US 2010/0331754 A1, 2009/0101577 A1, and US 2009/0076434 A1, which are incorporated herein by reference in their entireties, describe pressure measurements, volume control, ultrafiltration control, and other elements that can be used in accordance with the present invention. US 2010/0252490 A1, which is incorporated herein by reference in its entirety, describes a dialysate reservoir and other elements that can be used in accordance with the present invention. US 2010/0234786 A1, which is incorporated herein by reference in its entirety, describes a disconnection monitor and other elements that can be used in accordance with the present invention. US 2010/0184198 A1, which is incorporated herein by reference in its entirety, describes a method of ammonia removal and other elements that can be used in accordance with the present invention. US 2011/0315611 A1, US 2011/0054378 A1, US 2010/0140149 A1, and US 2009/0101552 A1, which are incorporated herein by reference in their entireties, describe a manifold, dialysis machine, dialysis system, and other elements that can be used in accordance with the present invention. US 2012/0073365 A1, US 2010/0116048 A1, and US 2009/0114037 A1, which are incorporated herein by reference in their entireties, describe flow meters and other elements that can be used in accordance with the present invention.

The extracorporeal circuit used in the method can include an arterial side and a venous side and the portion can be diverted into at least one of the arterial side and the venous side. The method can include measuring a central venous pressure of the patient. The flow restriction can be varied depending on the central venous pressure measured. The method can include determining a target volume of fluid to be added or removed from the patient. The flow restriction can be varied to add or remove the target volume. Blood can be pumped from the patient through the arterial line and through the tube section of the manifold and through the dialyzer back through the manifold and back to the patient. An initial supply of dialysate can be pumped to the manifold through an internal manifold passageway and tube section in operative communication with a tube section of the manifold.

In the present invention, a dialysis machine can perform a continuous hemofiltration (CHF) dialysis treatment utilizing the removed ultrafiltrate and initial small volume prime solution contained in a dialysis reservoir for the injection quality fluid used to provide the HDF treatment, thereby eliminating the need for additional fresh water or bagged solutions. For example, flow restrictors can be used to divert a portion of the dialysate flow through additional bacteria filters to the blood stream either pre or post dialyzer. For this closed system, the solution reaching the reservoir can be equal to both the dialysate flow and the HDF infused flow. Adjustments can be made by the dialysate pumps to accommodate for net ultrafiltration from the patient. Given that the initial prime volume can be small and no additional fluid needs to enter the system, the additional bacteria filters used for the injection (arterial and/or venous) side of the circuit can be minimal.

The present invention can use manifolds, disposables, dialysis machines, dialysis systems, methods or any other aspect of dialysis as described in U.S. Patent Application Publications Nos. US 2012/0280154 A1, US 2012/0204968 A1, US 2012/0103885 A1, US 2012/0090706 A1, US 2012/0073365 A1, US 2011/0315611 A1, US 2011/0054378 A1, US 2010/0331754 A1, US 2010/0252490 A1, US 2010/234786 A1, US 2010/0184198 A1, US 2010/0179464 A1, US 2010/0140149 A1, US 2010/0116740 A1, US 2010/0116048 A1, US 2009/0173682 A1, US 2009/0114037 A1, US 2009/0101577 A1, US 2009/0101552 A1, and US 2009/0076434 A1, each of which is incorporated herein by reference in its entirety.

Figure 2:
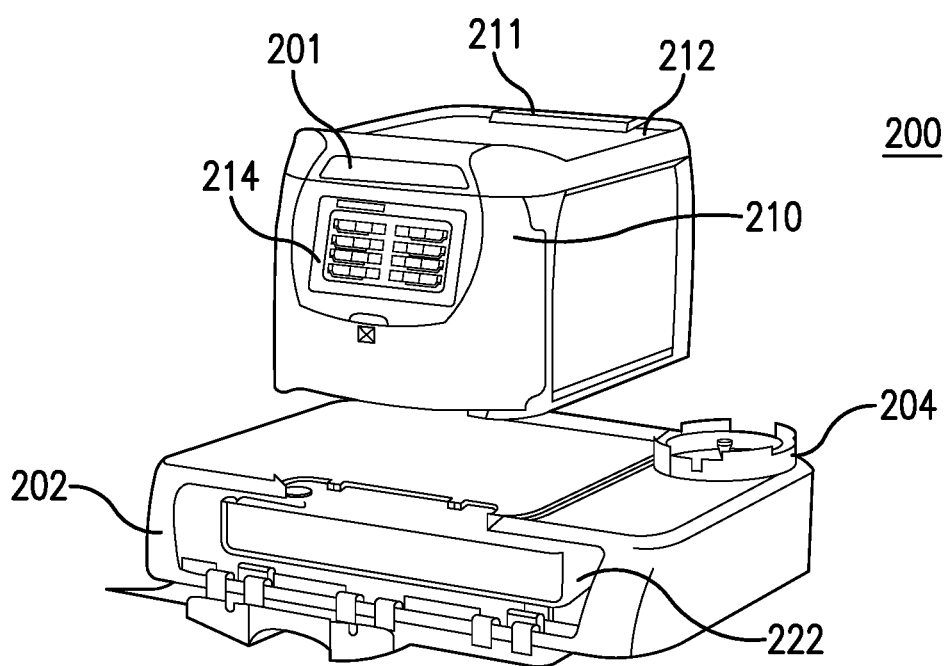
FIG. 2 is a right perspective view a dialysis system in accordance with the present invention, showing the modularity of the system.
Figure 3:
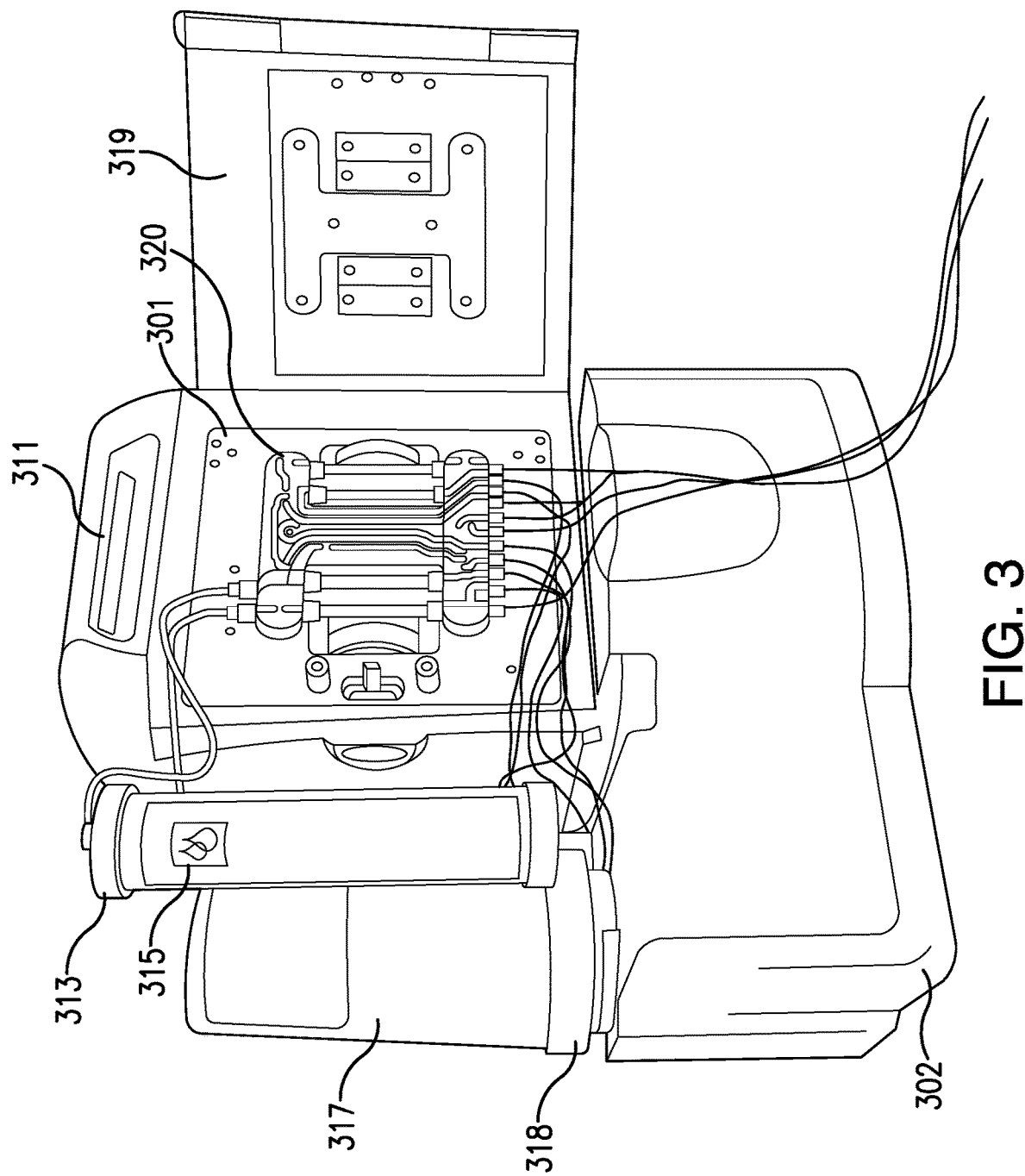
FIG. 3 is a left view of a dialysis system in accordance with the present invention, with the door open to show a manifold engaged with the system.

Referring to FIGS. 1, 2, and 3, the dialysis system 100, 200 includes a top unit 101, 201 that is detachably affixed to a base 102, 202. Base unit 102, 202 contains a reservoir 122, 222 for fluid storage, measurement, and monitoring. Top unit 101, 201, also referred to as the main unit or controller unit, includes a graphical user interface 114, 214, a pumping unit, and a door 110, 210 having a power lock. To a first side of top unit 101, 201, is a clasp 105 used to detachably affix a dialyzer 103, 313. Also to a side of top unit 101, 201, is a sorbent cartridge locking base 104, 204, 318, that is used to detachably affix a sorbent cartridge 107, 317. Clasp 105, hemofilter 103, 315, sorbent cartridge locking base 104, 204, 318 and sorbent cartridge 107, 317 can be positioned on the same side of top unit 101, as shown in FIG. 3, or on different sides or at different positions. In either case, base unit 102, 202, 302 can have a sufficiently larger top surface area relative to the top unit such that shelves can be formed on either side of the top unit to hold the sorbent cartridge, to hold an infusate jar, to capture any spillage, and/or to channel any leaks into a leak detector. With reference to FIG. 3, a door 319 is shown in an open position to reveal a manifold 320 mounted to the top unit 301. A handle 311 can be provided on top unit 301. The system configurations shown in FIGS. 1, 2, and 3 are exemplary and not limiting. For example, as shown in FIG. 3, top unit 301 can be positioned on one side of base unit 302, as opposed to being centrally positioned on top of base unit 302. Further details of suitable dialysis machines and components thereof, which can be used to carry out the methods of the present invention and form the systems of the present invention, are described, for example, in U.S. Patent Application Publication No. US 2011/0315611 A1, which is incorporated herein by reference in its entirety.

Figure 4:
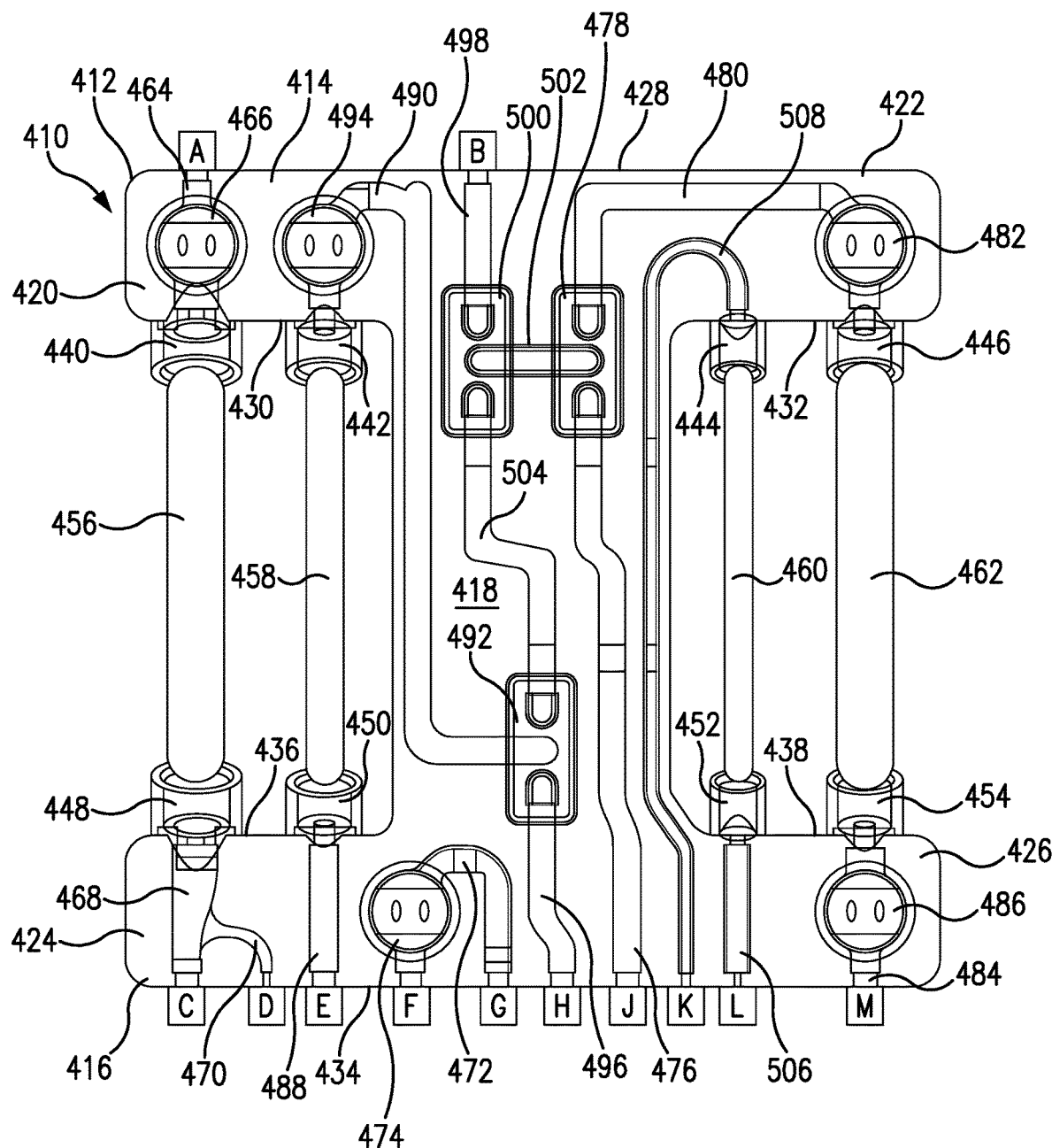
FIG. 4 is a front view of a manifold in accordance with the present invention.

With reference to FIG. 4, a manifold 410 can be provided that has a capital I-shaped body 412. Manifold body 412 can include a first transom 414 and a second transom 416 that are joined together by a central member or trunk 418. Both transoms can have first and second arms located on either side of trunk, for example, a first arm 420 can be on a left side of transom 414 and a second arm 422 can be on the right side of transom 414. Similarly, third and fourth arms 424, 426 can be on respective sides of second transom 416. First transom 414 can have first, second, and third edges 428, 430, and 432, respectively. First edge 428 spans first transom 414, and second edge 430 and third edge 432 are along first arm 420 and second arm 422, respectively. Second transom 416 can have fourth, fifth, and sixth edges, 434, 436, and 438, respectively. Fourth edge 434 spans second transom 416, and fifth edge 436 and sixth edge 438 are along third arm 424 and fourth arm 426, respectively.

Various conduits can be located in manifold body 412 and can be in fluid communication with valves, pressure sensor chambers, and other elements within manifold body 412 as well as being in fluid communication with one or more manifold ports on manifold body 412. The manifold ports can include intra-manifold ports and external ports. The intra-manifold ports can be joined by one or more pumping tube, and the external ports can fluidly connect the manifold to other portions of the dialysis machine and to the patient, via tubes. The tubes can be flexible. A flexible membrane or sheet can cover part of one or more sides of the manifold and can form part of the manifold body.

As depicted in FIG. 4, the external ports can be lettered from "A" to "M" (omitting "I"). The intra-manifold ports can be referred to by ordinal numbers, for example, 440, 442, 444, 446, 448, 450, 452, and 454. External ports A and B are shown along first edge 428 of first transom 414 and external ports C through M are arrayed along fourth edge 434 of second transom 416. First and second intra-manifold ports 440, 442 are arrayed along second edge 430 of first arm 420. Third and fourth intra-manifold ports 444, 446 are arrayed along third edge 432 of second arm 422. Fifth and sixth intra-manifold ports 448, 450 are arrayed along fifth edge 436 of third arm 424, and seventh and eighth intra-manifold ports 452, 454 are arrayed along sixth edge 438 of fourth arm 426. A first pumping tube 456 joins first and fifth intra-manifold ports 440, 448, respectively. A second pumping tube 458 joins second and sixth intra-manifold ports, 442, 450, respectively. A third pumping tube 460 joins third and seventh intra-manifold ports, 444, 452, fourth pumping tube 462 joins the fourth and eighth intra-manifold ports 446, 454, respectively.

A first conduit 464 can extend from external port A to first intra-manifold port 440 and can contain a first pressure sensor chamber 466. A second conduit 468 can extend from fifth intra-manifold port 448 to external port C. A third conduit 470 can branch off of second conduit 468 and extend to external port D. A fourth conduit 472 can extend between external port F and external port G, and can contain a second pressure sensor chamber 474. A fifth conduit 476 can extend from external port J to a first multivalve 478. A sixth conduit 480 can extend from first multivalve 478 to the fourth intra-manifold port 446, and can contain a third pressure sensor chamber 482. A seventh conduit 484 can extend from eighth intra-manifold port 454 to external port M, and can include a fourth pressure sensor chamber 486. An eighth conduit 488 can extend from external port E to sixth intra-manifold port 450. A ninth conduit 490 can extend from second intra-manifold port 442 to a second multivalve 492, and can include a fifth pressure sensor chamber 494. A tenth conduit 496 can extend from second multivalve 492 to external port H. An eleventh conduit 498 can extend from external port B to a third multivalve 500. A twelfth conduit 502 can connect third multivalve 500 to first multivalve 478, and a thirteenth conduit 504 can connect second and third multivalves 492, 500 respectively. A fourteenth conduit 506 can extend from external port L to seventh intra-manifold port 452. A fifteenth conduit 508 can extend from third intra-manifold port 444 to external port K. While certain conduits are described as containing a pressure sensor chamber, any conduit can contain any number of pressure sensor chambers. Each pressure sensor chamber can be independently covered by the flexible sheet and be aligned with a pressure sensor on a dialysis machine housing to allow for pressure measurements of a fluid with a given conduit. The multivalves can also be covered by the flexible sheet and can be aligned with actuators on a dialysis machine housing, the actuators being configured to control the multivalves and flow through the multivalves.

Figure 5:
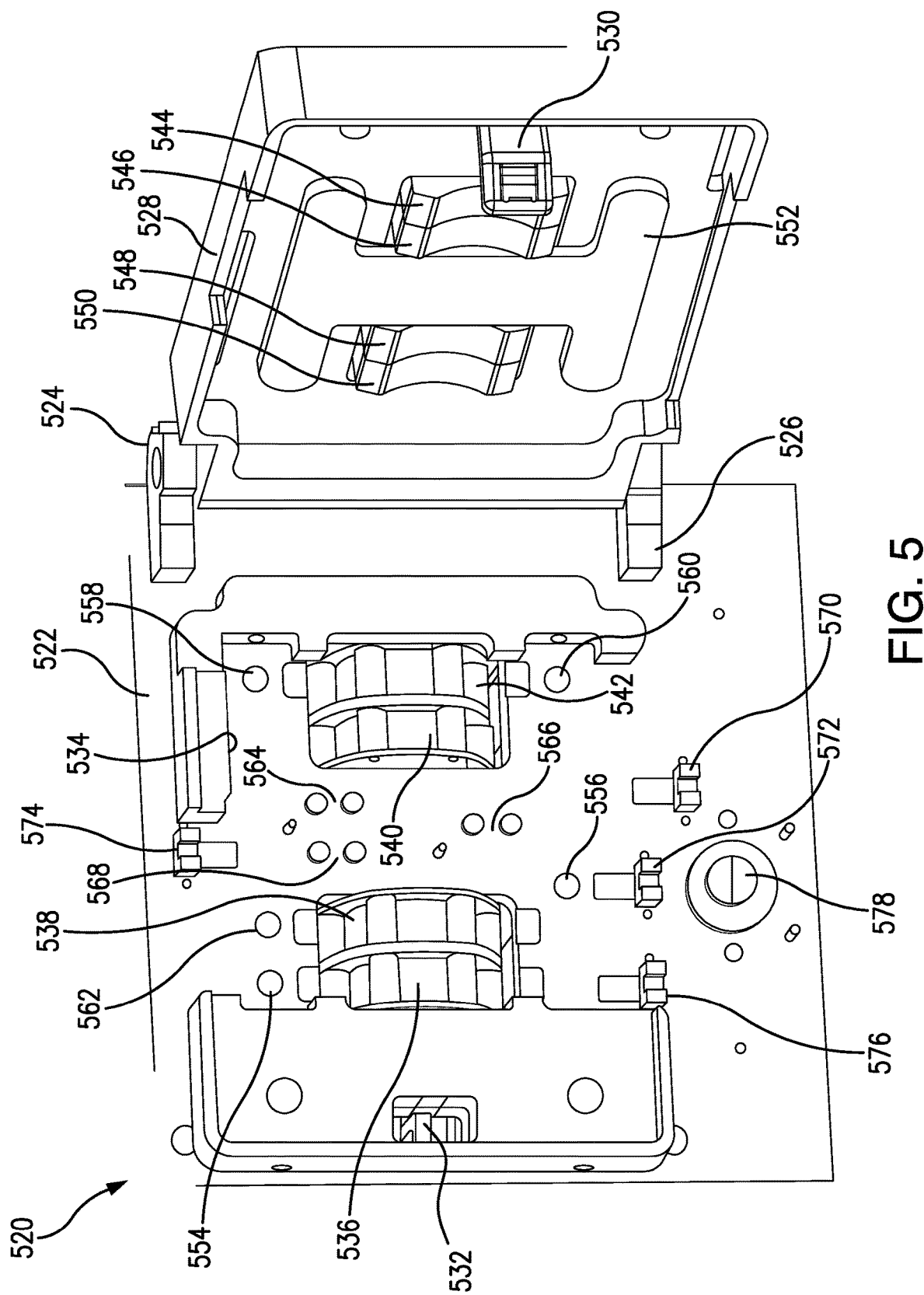
FIG. 5 is a left, perspective, close-up view of a dialysis system in accordance with the present invention, with the door open.

FIG. 5 is a partial view of a dialysis machine 520 in accordance with the present invention. Dialysis machine 520 has a machine housing 522 to which first and second hinges 524, 526, respectively, are mounted. A door 528 is, in turn, mounted to these hinges. Door 528 is shown in an open position in FIG. 5, but can be closed and secured with a door lock that includes a door lock insert 530 attached to door 528, and a door lock receptacle 532 disposed in machine housing 522. A manifold receptacle 534 is mounted on machine housing 522 and is configured to receive a manifold, for example, manifold 410 shown in FIG. 4. First, second, third, and fourth peristaltic pumps 536, 538, 540, and 542, respectively, are inset in machine housing 522 and positioned to engage first, second, third, and fourth pump tubes or pump headers, for example, pump tubes 456, 458, 460, and 462, shown in FIG. 4, respectively. First, second, third, and fourth pump shoes 544, 546, 548, and 550, respectively, are mounted on the inside of door 528 and are configured to press first, second, third, and fourth pump tubes of a manifold against first, second, third, and fourth peristaltic pumps 536, 538, 540, and 542, respectively. A platen 552 is also mounted on the inside of door 528 and is configured to press a manifold, for example, manifold 410, shown in FIG. 4, into manifold receptacle 534.

First, second, third, fourth, and fifth pressure sensors 554, 556, 558, 560, and 562, respectively, are positioned on machine housing 522 within manifold receptacle 534 to engage first, second, third, fourth, and fifth pressure sensor chambers 466, 474, 482, 486, and 494, shown in FIG. 4, respectively. A first set of valve actuators 564 is positioned in machine housing 522 within manifold receptacle 534, to engage first multivalve 478 shown in FIG. 4. A second set of valve actuators 566 is positioned in machine housing 522 within manifold receptacle 534 to engage second multivalve 492 shown in FIG. 4. A third set of valve actuators 568 is positioned in machine housing 522 within manifold receptacle 534 to engage third multivalve 500 shown in FIG. 4. First and second air detectors 570, 572 are included in machine housing 522. A blood leak detector 574, an occlusion detector 576, and a bloodline clamp 578, are also included in machine housing 522.

Figure 6:
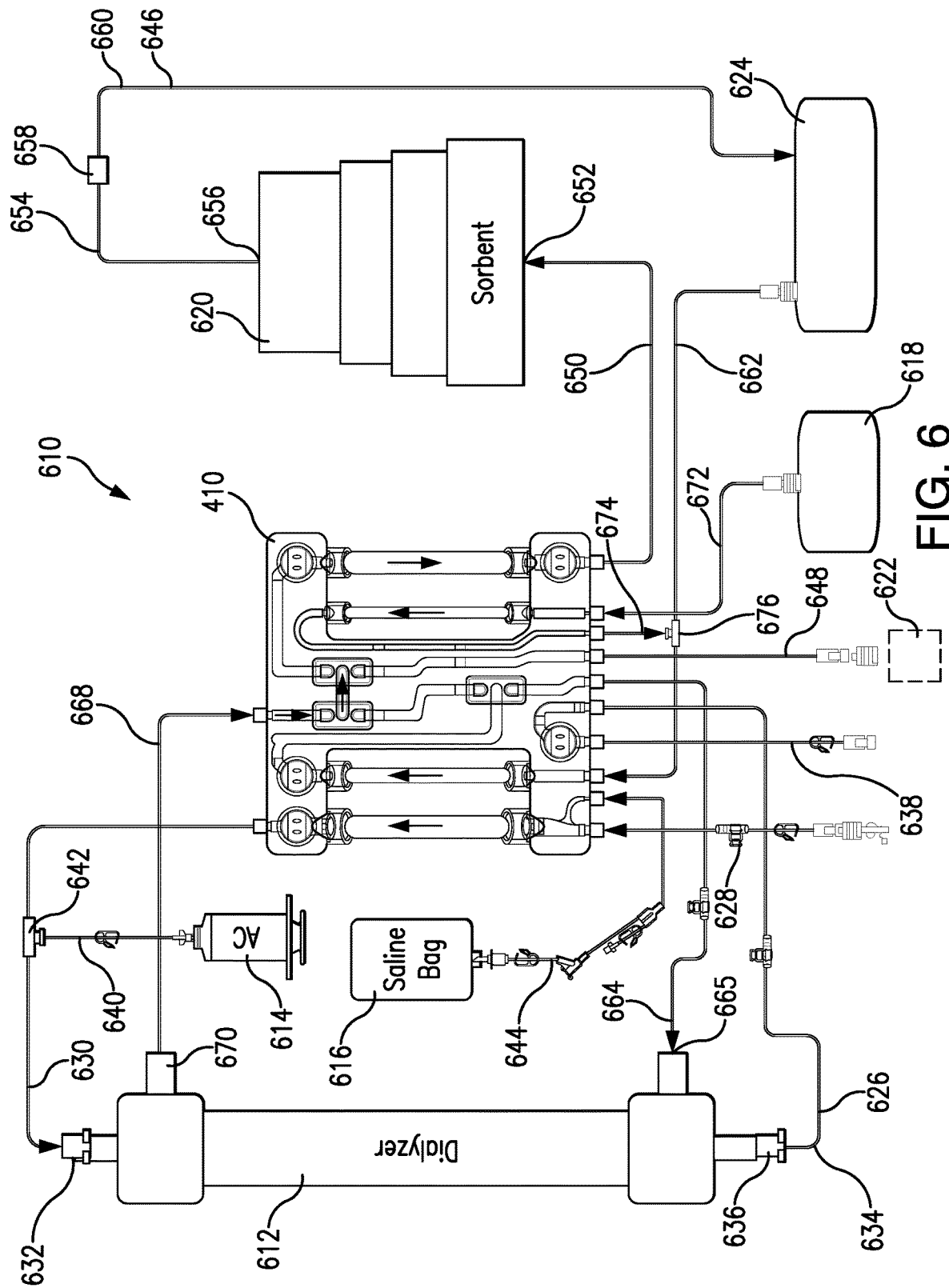
FIG. 6 is a schematic circuit diagram of a hemodialysis system in accordance with the present invention.

FIG. 6 shows a schematic diagram of a hemodialysis system 610 that can utilize a suitable manifold, for example, manifold 410, the details of which are shown in FIG. 4. External tubes, preferably flexible, are used to connect the manifold via the external ports to other components of the dialysis system, such as a dialyzer 612, an anticoagulant source 614, a saline source 616, an electrolyte source 618, a sorbent cartridge 620, a dialysate source 622, and a dialysate reservoir 624. Collectively, the manifold, external tubes, and other dialysis system components can form one or more circuits, for example, an extracorporeal blood circuit and a dialysate circuit. One can appreciate that a given tube can be made of one or more shorter tubes joined together by one or more connectors.

As can be seen in FIG. 6, an extracorporeal blood circuit 626 is provided in the hemodialysis system shown. A first external tube 628 can extend from the patient, for example, an artery of the patient, to external port C. A second external tube 630 can extend from external port A to a first dialyzer port 632. A third external tube 634 can extend from a second dialyzer port 636 to external port G. A fourth external tube 638 can extend from external port F back to the patient, for example, to a vein of the patient. A fifth external tube 640 can connect anti-coagulant source 614 to the extracorporeal blood circuit 626, for example, at a first branch point 642 in second external tube 630. A sixth external tube 644 can connect saline source 616 to external port D.

With reference to FIGS. 4-6, blood can flow in extracorporeal blood circuit 626 in the following manner. The flow can be powered and controlled by first peristaltic pump 536, shown in FIG. 5, operatively associated with first pump tube 456, shown in FIG. 4. Blood can flow from the patient, for example, out of an artery, through first external tube 628, through second conduit 468, first pump tube 456, through first conduit 464, through second external tube 630, through dialyzer 612, through third external tube 634, through fourth conduit 472, through fourth external tube 638, and back to the patient, for example, into a vein of the patient. Anticoagulant can be supplied through fifth external tube 640 into extracorporeal blood circuit 626. A priming sequence can be used in extracorporeal blood circuit 626 by flowing saline from saline source 616 through external tube 644 and third conduit 470 into extracorporeal blood circuit 626, for example, at a location along second conduit 468.

A dialysate circuit 646 can also form part of hemodialysis system 610. A seventh external tube 648 can extend from a dialysate or water source 622 to external port J. An eighth external tube 650 can extend from external port M to a first sorbent cartridge port 652. A ninth external tube 654 can extend from a second sorbent cartridge port 656 to an ammonia sensor 658. A tenth external tube 660 can extend from ammonia sensor 658 to dialysate reservoir 624. An eleventh external tube 662 can extend from dialysate reservoir 624 to external port E. A twelfth external tube 664 can extend from external port H to a third dialyzer port 665. A thirteenth external tube 668 can extend from a fourth dialyzer port 670 to external port B. A fourteenth external tube 672 can extend from electrolyte source 618 to external valve port L. A fifteenth external tube 674 can extend from external port K to a second branch point 676 in eleventh external tube 662.

As can be seen in FIGS. 4-6, dialysate can flow through dialysate circuit 646, which can be powered by second and fourth peristaltic pumps 538, 542, respectively, shown in FIG. 5, which are in operative association with second and fourth pump tubes 458, 462, respectively, shown in FIG. 4. Third peristaltic pump 540 can be in operative association with third pump tube 460 to allow a flow of electrolytes to enter dialysate circuit 646. Dialysate, or water, can flow from dialysate source 622 through seventh external tube 648, fifth conduit 476, sixth conduit 480, fourth pump tube 462, seventh conduit 484, eighth external tube 650, sorbent cartridge 620, ninth external tube 654, ammonia sensor 658, tenth external tube 660, dialysate reservoir 624, eleventh external tube 662, eighth conduit 488, second pump tube 458, ninth conduit 490, tenth conduit 496, twelfth external tube 664, dialyzer 612, thirteenth external tube 668, eleventh conduit 498, twelfth conduit 502, and back to sixth conduit 480, to complete dialysate circuit 646. Electrolytes can flow through fourteenth external tube 672, fourteenth conduit 506, pump tube 460, fifteen conduit 508, and into dialysis circuit 646, for example, at second branch point 676 along eleventh external tube 662.

Figure 7A:
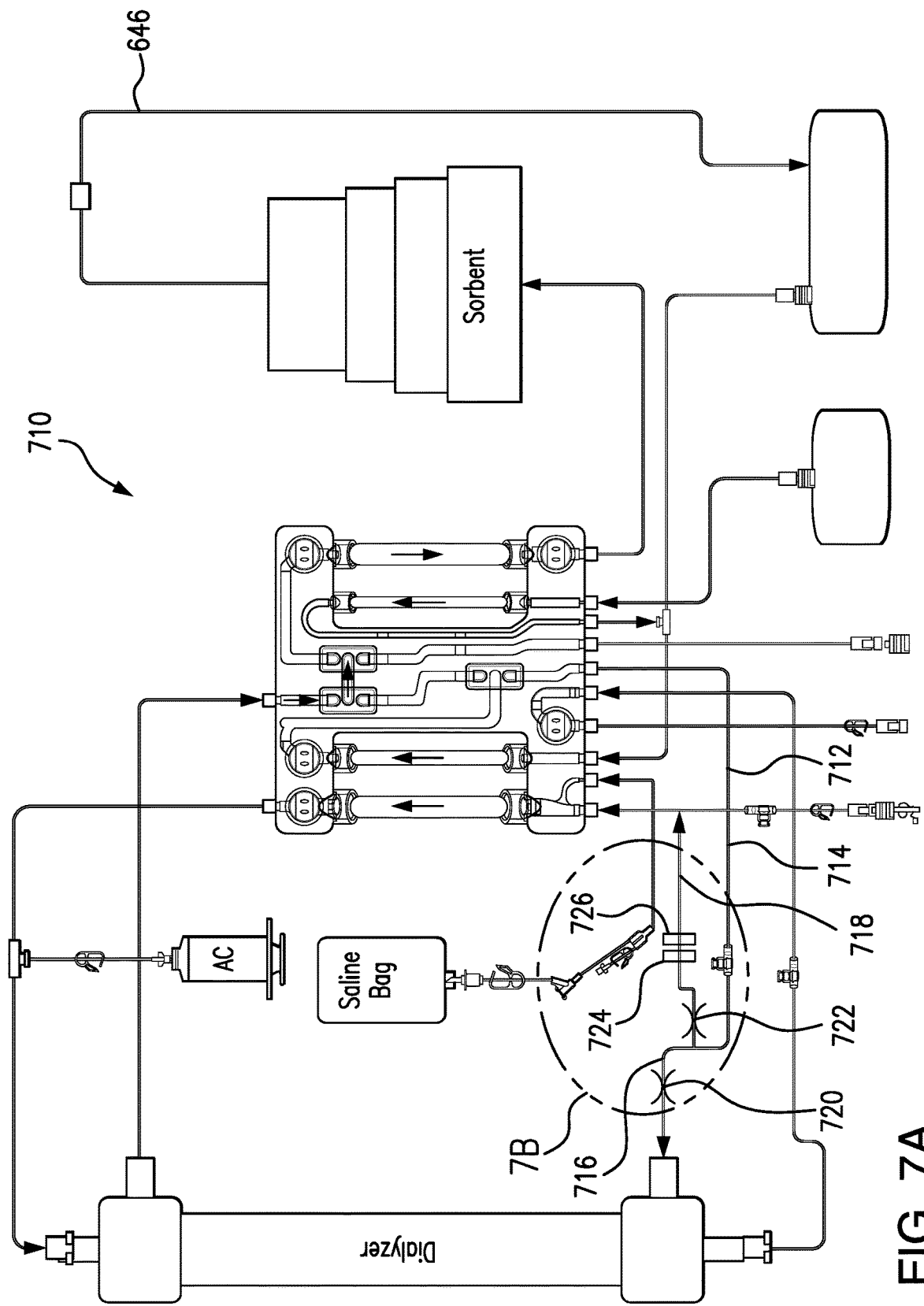
FIG. 7A is a schematic circuit diagram of a hemodiafiltration system in accordance with the present invention.

FIG. 7A shows a hemodiafiltration system 710 that represents a significant advancement over hemodialysis system 610 shown in FIG. 6. A sixteenth external tube 712 replaces external tube 664 and is placed in fluidic communication with both extracorporeal blood circuit 626 and dialysate circuit 646. Sixteenth external tube 712 is shown in greater detail in FIG. 7B. Sixteenth external tube 712 can link dialysate circuit 646 to first and/or second external tubes 628, 630 on an arterial side of the extracorporeal blood circuit. Alternatively, or additionally, sixteenth external tube 712 can join dialysate circuit 646 and third and/or fourth external tubes 634 and/or 638, respectively, on the venous side of extracorporeal blood circuit 626. The dialysate flow can originate from a main segment 714 and be split between a first branch segment 716 and a second branch segment 718.

The proportion of dialysate remaining in dialysate circuit 646 to that entering extracorporeal blood circuit 626 in hemodiafiltration system 710 can be controlled by any suitable mechanism. For example, one or more flow restrictors can be used. A flow restrictor can be located in and/or on at least one of first branch segment 716 and second branch segment 718. For example, a first flow restrictor 720 can be located in and/or on first branch segment 716 and a second flow restrictor 722 can be located in and/or on second branch segment 718. A flow restrictor can have a defined or a variable restriction. A flow restrictor can be formed as part of the external tube. A flow restrictor can be distinct from, but operatively connectable to, the external tube. A flow restrictor can be provided on a dialysis machine housing and be configured to accept an external tube. Any suitable flow restrictor can be used. For example, a flow restrictor can be clipped on the outside of the external tube. One or more valve can act as a flow restrictor. One or more additional pumps and/or valves can be used in place of or in addition to the at least one flow restrictor. For example, a two-way valve that opens and closes periodically can be used to achieve a diversion of flow. Flow diversion can be achieved by simply using a branched external line independent of any induced restriction.

Figure 7B:
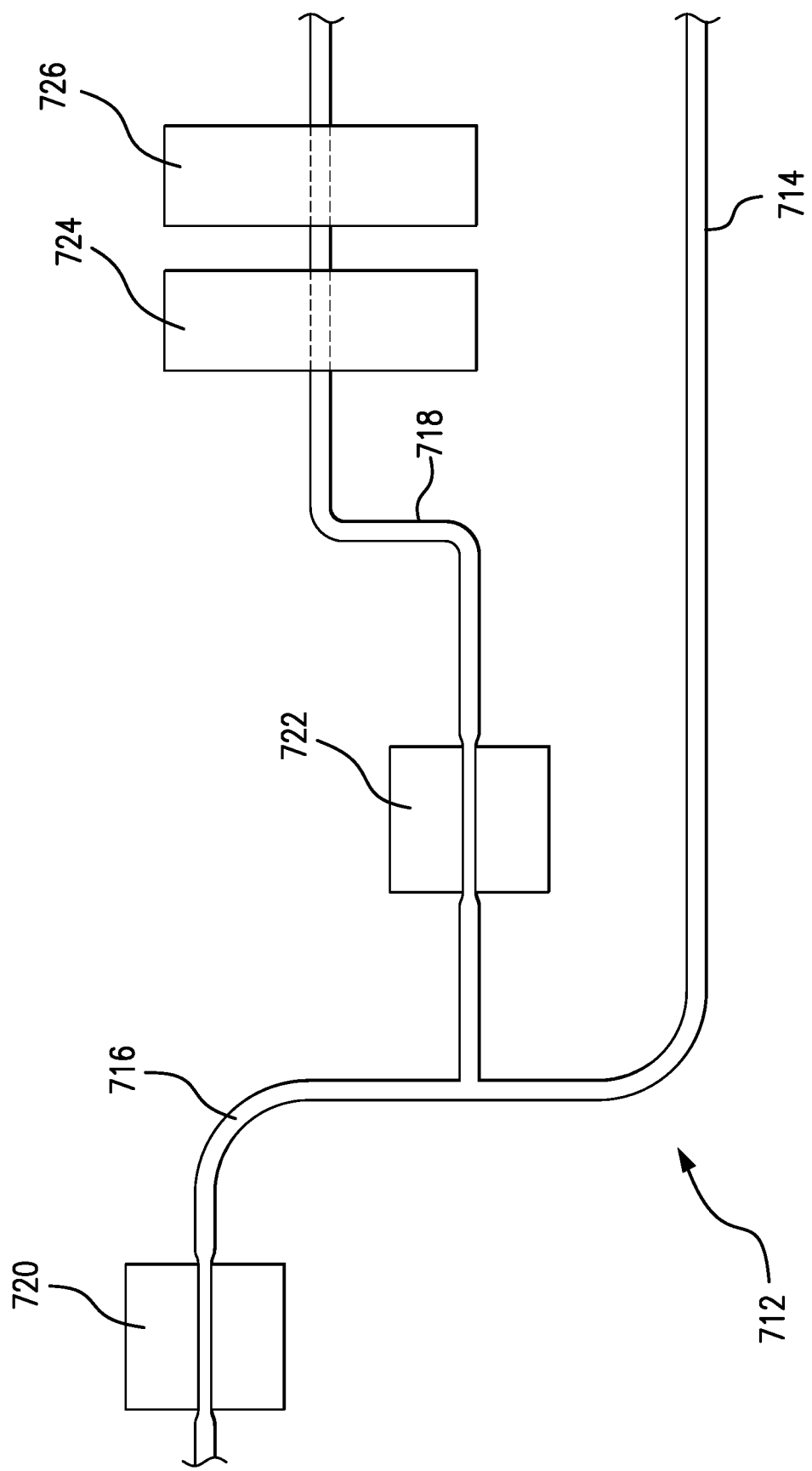
FIG. 7B is an enlargement of a portion of the hemodiafiltration system shown in FIG. 7A.

Sixteenth external tube 712 can contain one or more bacterial filter in parallel and/or in series with one another. Any suitable number or type of bacterial filter can be used. The at least one bacterial filter can be placed at any suitable location. For example, FIGS. 7A and 7B show a first bacterial filter 724 and a second bacterial filter 726 in second branch segment 718. A bacterial filter can also act as or as part of a flow restrictor.

Figure 8:
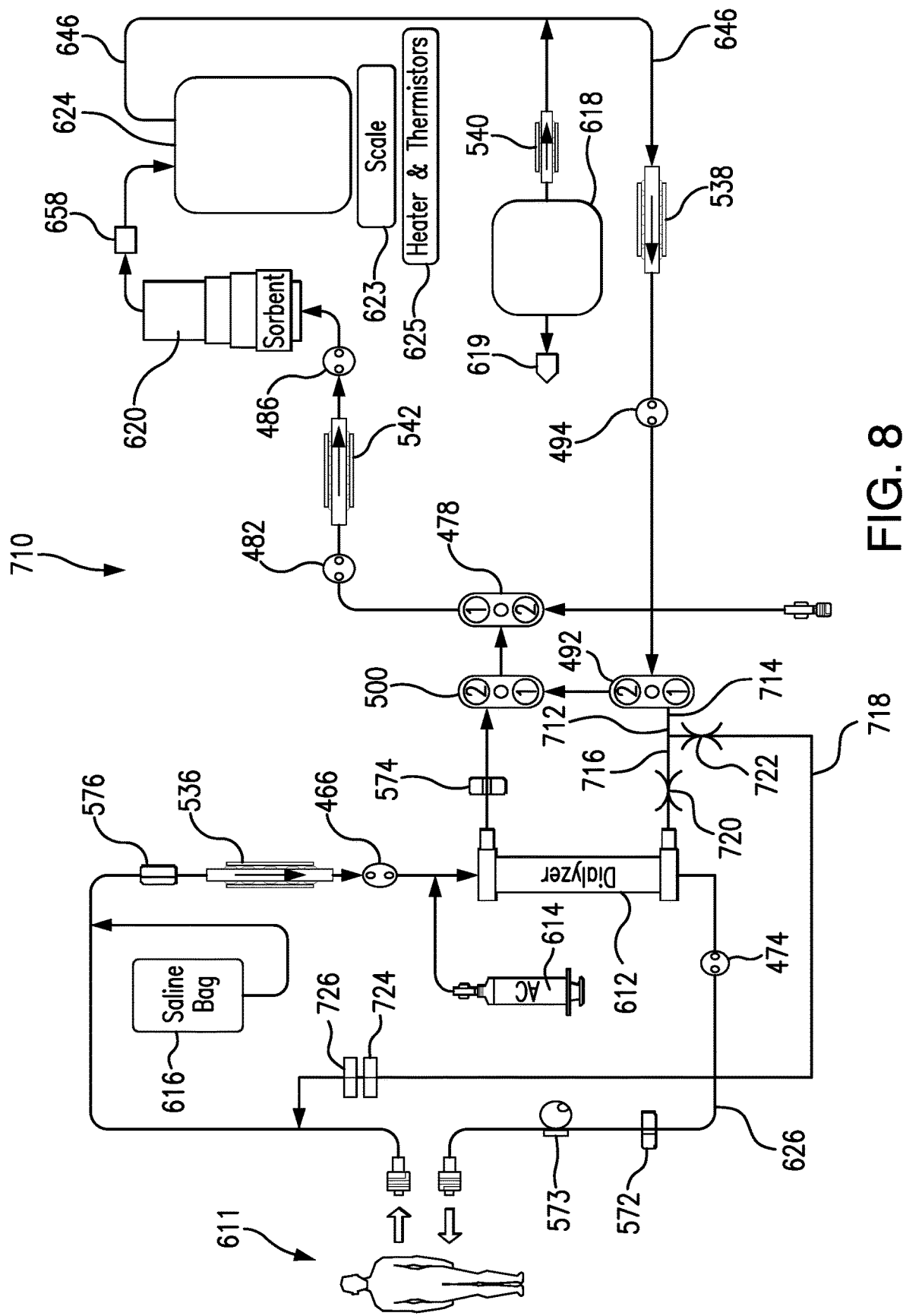
FIG. 8 is a schematic flow diagram of the schematic circuit diagram shown in FIG. 7A.

FIG. 8 is a schematic flow diagram of hemodiafiltration system 710 shown in FIG. 7A, which also refers to elements identified in FIGS. 4-6. Blood can be pumped, from a patient 611, by first peristaltic pump 536 and be made to flow through extracorporeal blood circuit 626, through occlusion detector 576, through first pressure sensor chamber 466, through dialyzer 612, through second pressure sensor chamber 474, through second air detector 572, through pinch valve 573, and back to patient 611. An anticoagulant source 614 can be used to add anticoagulant into extracorporeal blood circuit 646. Saline source 616 can be used to prime extracorporeal blood circuit 626. Dialysate can be pumped into dialysate circuit 646 by second and fourth peristaltic pumps, 538 and 542 respectively, through first multivalve 478, through third pressure sensor chamber 482, through fourth pressure sensor chamber 486, through sorbent cartridge 620, through ammonia sensor 658, through dialysate reservoir 624, through fifth pressure sensor 494, and through second multivalve 492. After passing through second multivalve 492 and into sixteenth external tube 712, the dialysate can flow into first branch segment 716 and/or second branch segment 718, which can be controlled by first and/or second flow restrictors 720 and/or 722, respectively. Dialysate flowing through second branch segment 718 can flow through first and second bacterial filters 724, 726, before flowing into extracorporeal blood circuit 626. Electrolytes can be pumped from electrolyte source 618 that can be monitored with a level sensor 619. The electrolytes can be pumped, using a third peristaltic pump 540, into dialysate circuit 646. Dialysate in dialysate reservoir 624 can be weighed by a scale 623 and heated using heater/thermistors 625.

Switching between a hemodialysis mode and a hemodiafiltration mode can be achieved by switching between appropriate sets of disposables, although the core manifold design can be maintained in both modes. A switch to or from a peritoneal dialysis mode can be similarly accomplished in accordance with the present invention. A switch between a hemodialysis mode and a hemodiafiltration mode can also be achieved by using the same set of disposables together with a complete restriction and or valve rerouting of circuit flows.

The present invention includes the following aspects/embodiments/features in any order and/or in any combination:

1. A manifold comprising:
    a manifold body comprising
        at least one conduit comprising a first conduit
        at least one port comprising a first port in fluid communication with the first conduit;
        an external tube in fluid communication with the first port and comprising
            a main segment,
            a first branch segment comprising a first flow restrictor, and
            a second branch segment comprising a second flow restrictor and at least one bacterial filter,
        wherein the second flow restrictor is located between the at least one bacterial filter and the main segment.
2. The manifold of any preceding or following embodiment/feature/aspect, wherein the second branch segment comprises at least two bacterial filters.
3. The manifold of any preceding or following embodiment/feature/aspect, further comprising a dialyzer in fluid communication with the first branch segment.
4. The manifold of any preceding or following embodiment/feature/aspect, wherein at least one of the first and second flow restrictors comprises a static flow restrictor.
5. The manifold of any preceding or following embodiment/feature/aspect, wherein the manifold is configured to engage a dialysis machine and the first conduit is configured to join a first circuit.
6. The manifold of any preceding or following embodiment/feature/aspect, wherein the dialysis machine comprises at least one pump and the manifold is configured to engage the at least one pump to allow for movement of a first fluid through the first circuit.
7. The manifold of any preceding or following embodiment/feature/aspect, wherein the at least one pump comprises a peristaltic pump.
8. The manifold of any preceding or following embodiment/feature/aspect, wherein the manifold comprises a second conduit configured to join a second circuit.
9. The manifold of any preceding or following embodiment/feature/aspect, wherein the dialysis machine comprises a second pump and the manifold is configured to engage the second pump to allow for movement of a second fluid in the second circuit.
10. The manifold of any preceding or following embodiment/feature/aspect, wherein the external tube is in fluid communication with the first and second conduits.
11. The manifold of any preceding or following embodiment/feature/aspect, wherein the second branch segment comprises a valve between the at least one bacterial filter and the main segment.
12. The manifold of any preceding or following embodiment/feature/aspect, wherein the first circuit is a dialysate circuit and the second circuit is an extracorporeal blood circuit.
13. A kit comprising the manifold of any preceding or following embodiment/feature/aspect and a dialyzer.
14. A dialysis machine comprising:
    a housing;
    a receptacle mounted on the housing and configured to accept the manifold of any preceding or following embodiment/feature/aspect; and
    the manifold of any preceding or following embodiment/feature/aspect operatively engaged with the receptacle.
15. A dialysis system comprising:
    the dialysis machine of any preceding or following embodiment/feature/aspect; and
    a supply of dialysate in fluid communication with the manifold;
    wherein the dialysis system is configured to perform hemodiafiltration.
16. A dialysis machine comprising:
    a housing;
    a receptacle mounted on the housing and configured to accept a manifold
    the manifold operatively engaged with the receptacle, the manifold comprising
        a manifold body comprising
            at least one conduit comprising a first conduit
            at least one port comprising a first port in fluid communication
            with the first conduit;
            an external tube in fluid communication with the first port and comprising
                a main segment,
                a first branch segment, and
                a second branch segment comprising at least one bacterial filter; and
        at least one flow restrictor mounted on the housing and configured for accepting at least one of the first branch segment and the second branch segment.
17. The dialysis machine of any preceding or following embodiment/feature/aspect, wherein the at least one flow restrictor comprises a first flow restrictor configured to receive the first branch segment and a second flow restrictor configured to receive the second branch segment.
18. The dialysis machine of any preceding or following embodiment/feature/aspect, wherein the at least one flow restrictor comprises a static flow restrictor.

19. The dialysis machine of any preceding or following embodiment/feature/aspect, wherein the at least one flow restrictor comprises a dynamic flow restrictor.
20. A dialysis system comprising:
    the dialysis machine of any preceding or following embodiment/feature/aspect; and
    a supply of dialysate in fluid communication with the manifold;
    wherein the dialysis system is configured to perform hemodiafiltration.
21. A manifold comprising:
    a manifold body comprising
        a first transom comprising a first edge, and second and third edges substantially parallel to the first edge,
        a trunk substantially perpendicular to and adjacent the first transom,
        a second transom comprising a fourth edge, and fifth and sixth edges substantially parallel to the first, second, and third edges, the second transom being substantially perpendicular to and adjacent the trunk and substantially parallel to the first transom;
    a plurality of ports arrayed along the fourth edge, and comprising
        at least a first port and a second port,
        a third port located on the second edge, and
        a fourth port located on the fifth edge;
    a first conduit in the second transom and in fluid communication with the first and fourth ports,
    a second conduit in the first transom and in fluid communication with the second and third ports;
    a first pump tube in fluid communication with the third and fourth ports; and
    a first external tube in fluid communication with the second port and comprising
        a main segment,
        a first branch segment, and
        a second branch segment.
22. The manifold of any preceding or following embodiment/feature/aspect, wherein at least one of the first branch segment and the second branch segment comprises a flow restrictor.
23. The manifold of any preceding or following embodiment/feature/aspect, wherein the first branch segment comprises a first flow restrictor and the second branch segment comprises a second flow restrictor.
24. The manifold of any preceding or following embodiment/feature/aspect, wherein the flow restrictor is a static flow restrictor.
25. The manifold of any preceding or following embodiment/feature/aspect, wherein the second branch segment comprises at least one bacterial filter.
26. The manifold of any preceding or following embodiment/feature/aspect, wherein the second branch segment comprises a valve between the at least one bacterial filter and the main segment.
27. The manifold of any preceding or following embodiment/feature/aspect, further comprising a dialyzer in fluid communication with the first branch segment.
28. The manifold of any preceding or following embodiment/feature/aspect, wherein the manifold is configured to engage a dialysis machine and the first conduit is configured to join a first circuit.
29. The manifold of any preceding or following embodiment/feature/aspect, wherein the dialysis machine comprises at least one pump and the manifold is configured to engage the at least one pump with the first pump tube to allow for a movement of a first fluid in the first circuit.
30. The manifold of any preceding or following embodiment/feature/aspect, wherein the at least one pump comprises a peristaltic pump.
31. The manifold of any preceding or following embodiment/feature/aspect, wherein the manifold comprises a second pump tube in fluid communication with a fifth port on the second edge and a sixth port on the fifth edge, the second pump tube being configured to join a second circuit, wherein the dialysis machine comprises a second pump and the manifold is configured to engage the second pump with the second pump tube to allow for movement of a second fluid through the second circuit.
32. The manifold of any preceding or following embodiment/feature/aspect, wherein the external tube is in fluid communication with the first and second circuits.
33. The manifold of any preceding or following embodiment/feature/aspect, wherein the first circuit is a dialysate circuit and the second circuit is an extracorporeal blood circuit.
34. A kit comprising:
    the manifold of any preceding or following embodiment/feature/aspect,
    a dialyzer; and
    a bacterial filter.
35. A dialysis system comprising:
    a dialysis machine;
    the manifold of any preceding or following embodiment/feature/aspect operatively engaged with the dialysis machine; and
    a supply of dialysate in fluid communication with the manifold;
    wherein the second branch segment comprises at least one bacterial filter and the dialysis system is configured to perform hemodiafiltration.
36. A method of performing hemodiafiltration on a patient comprising:
    pumping a flow of dialysate through a dialysate circuit;
    pumping a flow of blood through an extracorporeal blood circuit;
    restricting the flow of dialysate in the dialysate circuit to divert a portion of the flow of dialysate into the extracorporeal blood circuit; and
    passing the portion through at least one bacterial filter before the portion enters the blood circuit.
37. The method of any preceding or following embodiment/feature/aspect, wherein the flow restriction is static.
38. The method of any preceding or following embodiment/feature/aspect, wherein the flow restriction is varied.
39. The method of any preceding or following embodiment/feature/aspect, wherein the dialysate circuit comprises a branched conduit comprising a main segment, a first branch segment, and a second branch segment, wherein the second branch segment carries the portion and is in fluid communication with the extracorporeal blood circuit and the restricting comprises restricting the flow of dialysate in at least one of the first branch segment and the second branch segment.
40. The method of any preceding or following embodiment/feature/aspect, wherein the restricting comprises restricting the flow of dialysate in both the first branch segment and the second branch segment.
41. The method of any preceding or following embodiment/feature/aspect, wherein at least one of the flow of dialysate and the flow of blood is pumped through a manifold engaged with a dialysis machine.

42. The method of any preceding or following embodiment/feature/aspect, further comprising engaging the manifold with the dialysis machine.

43. The method of any preceding or following embodiment/feature/aspect, wherein at least one of the pumping the flow of dialysate and the pumping the flow of blood comprises pumping with at least one peristaltic pump.

44. The method of any preceding or following embodiment/feature/aspect, wherein the dialysate circuit comprises a sorbent cartridge capable of regenerating the dialysate.

45. The method of any preceding or following embodiment/feature/aspect, further comprising pumping an electrolyte solution into the dialysate circuit.

46. The method of any preceding or following embodiment/feature/aspect, wherein the pumping of the flow of dialysate and the pumping of the flow of blood comprises pumping through at least one dialyzer.

47. The method of any preceding or following embodiment/feature/aspect, wherein the at least one bacterial filter comprises at least one dialyzer.

48. The method of any preceding or following embodiment/feature/aspect, wherein the extracorporeal circuit comprises an arterial side and a venous side and the portion is diverted into at least one of the arterial side and the venous side.

49. The method of any preceding or following embodiment/feature/aspect, wherein the portion is diverted into the arterial side.

50. The method of any preceding or following embodiment/feature/aspect, further comprising measuring a central venous pressure of the patient.

51. The method of any preceding or following embodiment/feature/aspect, wherein the flow restriction is varied depending on the central venous pressure measured.

52. The method of any preceding or following embodiment/feature/aspect, further comprising determining a target volume of fluid to be added or removed from the patient.

53. The method of any preceding or following embodiment/feature/aspect, wherein the flow restriction is varied to add or remove the target volume.

The present invention can include any combination of these various features or embodiments above and/or below as set-forth in sentences and/or paragraphs. Any combination of disclosed features herein is considered part of the present invention and no limitation is intended with respect to combinable features.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A manifold comprising:
a manifold body comprising
a first transom comprising a first edge, and second and third edges substantially parallel to the first edge,
a trunk substantially perpendicular to and adjacent the first transom,
a second transom comprising a fourth edge, and fifth and sixth edges substantially parallel to the first, second, and third edges, the second transom being substantially perpendicular to and adjacent the trunk and substantially parallel to the first transom;
a first external port and a second external port located on the fourth edge,
a first intra-manifold port located on the second edge,
a second intra-manifold port located on the second edge,
a third intra-manifold port located on the fifth edge, and
a fourth intra-manifold port located on the fifth edge;
a first conduit in the second transom and in fluid communication with the second external port and the third intra-manifold port;
a second conduit in the manifold body and in fluid communication with both the second intra-manifold port and the first external port;
a first pump tube connected to and in fluid communication with the first and third intra-manifold ports;
a second pump tube connected to and in fluid communication with the second and fourth intra-manifold ports;
a first external tube connected to and in fluid communication with the first external port and comprising an external main segment, a first external branch segment, and a second external branch segment; and
an external blood tube in fluid communication with and extending from the second external port,
wherein the external main segment is connected to the first external port, the first external branch segment is connected to the external main segment and is configured to be connected to a dialyzer, the second external branch is connected to the external main segment and is in fluid communication with the external blood tube upstream of the first pump tube, and the entire manifold comprises disposable components.

2. The manifold of claim 1, wherein at least one of the first external branch segment and the second external branch segment comprises a flow restrictor.

3. A dialysis machine comprising the manifold of claim 1, wherein the manifold is configured to engage the dialysis machine and the first conduit is configured to join a first circuit.

4. The dialysis machine of claim 3, wherein the dialysis machine comprises at least one pump and the manifold is configured to engage the at least one pump with the first pump tube to allow for a movement of a first fluid in the first circuit.

5. The dialysis machine of claim 4, wherein the second pump tube is configured to join a second circuit, the dialysis machine comprises a second pump, and the manifold is configured to engage the second pump with the second pump tube to allow for movement of a second fluid through the second circuit.

6. A dialysis system comprising:
the dialysis machine of claim 5, wherein the manifold is operatively engaged with the dialysis machine; and
a supply of dialysate in fluid communication with the manifold;

wherein the second external branch segment comprises at least one bacterial filter and the dialysis system is configured to perform hemodiafiltration.

\* \* \* \* \*